(12) United States Patent
Siekmeier et al.

(10) Patent No.: US 7,945,392 B2
(45) Date of Patent: May 17, 2011

(54) METHODS AND SYSTEMS FOR DRUG SCREENING AND COMPUTATIONAL MODELING BASED ON BIOLOGICALLY REALISTIC NEURONS

(75) Inventors: Peter Siekmeier, Cambridge, MA (US); Steven Matthysse, Sudbury, MA (US)

(73) Assignee: McLean Hospital Corporation, Belmont, MA (US)

( * ) Notice: Subject to any disclaimer, the term of this patent is extended or adjusted under 35 U.S.C. 154(b) by 798 days.

(21) Appl. No.: 11/559,611

(22) Filed: Nov. 14, 2006

(65) Prior Publication Data

US 2008/0027651 A1 Jan. 31, 2008

Related U.S. Application Data

(60) Provisional application No. 60/736,599, filed on Nov. 14, 2005.

(51) Int. Cl.
*G06F 19/00* (2011.01)
*G06F 9/44* (2006.01)
*G06F 9/45* (2006.01)
*G06F 15/00* (2006.01)
*G11C 17/00* (2006.01)

(52) U.S. Cl. ................ 702/19; 703/21; 703/22; 365/94; 700/1

(58) Field of Classification Search ........................ None
See application file for complete search history.

(56) References Cited

U.S. PATENT DOCUMENTS

2006/0089824 A1 4/2006 Siekmeier et al.

OTHER PUBLICATIONS

Madeja et al. Reduction of voltage-operated potassium currents by levetiracetam: a novel antiepileptic mechanism of action? Neuropharmacology vol. 45, pp. 661-671 (2003).*
Lytton (1997) Computer model of clonazepam's effect in thalamic slice. Neuroreport vol. 8, 3339-3343 (1997).*
Treiman GABAergic Mechanisms in Epilepsy. Epilepsia vol. 42, pp. 8-12 (2001).*
Craig et al. Selective clustering of glutamate and gamma-aminobutyric acid receptors opposite terminals releasing the corresponding neurotransmitters. vol. 91, pp. 12373-12377 (1994).*
Krishek et al. A Functional Comparison of the Antagonists Bicuculline and Picrotoxin at Recombinant GABAa receptors. Neuropharmacology vol. 35, pp. 1289-1298 (1996).*
Aakerlund et al., "Neural networks as models of psychopathology," Biological Psychiatry, (43):471-482 (1998).
Bower, J.M. and D. Beeman, "The book of Genesis: exploring realistic neural models with the General Neural Simulation System," Springer-Verlag/Telos, (1998).
Brunello et al., "New insights into the biology of schizophrenia through the mechanism of action of clozapine," Neuropsychopharmacology, (13):177-213 (1995).
Kenakin, T., "Pharmacologic Analysis of Drug-Recepter Interaction," New York:Lippincott-Raven, 18-22 (1997).
Lytton et al., "Computer models of hippocampal circuit changes of the kindling model of epilepsy," Artifical Intelligence in Medicine, (13):81-97 (1998).
McGlashan et al., "Schizophrenia as a disorder of developmentally reduced synaptic connectivity," Archives of General Psychiatry, (57):637-648 (2000).
Siekmeier, P.J. and R. E. Hoffman, "Enhanced semantic priming in schizophrenia: a computer model based on excessive pruning of local connections in association cortex," British Journal of Psychiatry, (180):345-350 (2002).
Thomas et al., "Computer model of antiepileptic effects mediated by alterations in GABAa-mediated inhibition," Neuroreport, (9):691-696 (1998).
Thomas et al., "Increased synchrony with increase of a low-threshold calcium conductance in a model thalamic network: A phase-shift mechanism," Neural Computation, (12):1553-1571 (2000).
Tsubokawa, H., "Control of Na+ spike backpropagation by intracellular signaling in the pyramidal neuron dendrites," Molecular Neurobiology, 22(1-3):129-141 (2000).
Office Action, in U.S. Appl. No. 10/515,458, mailed Sep. 10, 2008.
Office Action, in U.S. Appl. No. 10/515,458, mailed Mar. 16, 2009.

* cited by examiner

*Primary Examiner* — John S Brusca
(74) *Attorney, Agent, or Firm* — Fish & Richardson P.C.

(57) ABSTRACT

A method for screening a test composition for potential efficacy in treatment of a disorder includes a first computer model representative of a volume of disease-afflicted neural tissue comprising biologically realistic neurons exposed to the test composition; and providing an initial excitation to the first computer model. Following a selected computation interval, a first outcome is determined. The first outcome indicates a response of the first computer model to the initial excitation and indicates whether the test composition has the potential to be effective in treating the disorder.

9 Claims, 28 Drawing Sheets

```
# ORIGINAL_SOURCE Neurolucida
# CREATURE rat F344
# REGION Hippocampus
# FIELD/LAYER CA1
# TYPE CA1 Pyramidal Cell in vivo young
# CONTRIBUTOR Buzsaki_G & Turner_DA
# REFERENCE J. Comp. Neurol. 391: 335-352, 1998
# RAW N402.asc
# EXTRAS Turner_P.CA1
# SOMA_AREA 0.30E3
# SHRINKAGE_CORRECTION 1.33 1.33 4.00
# VERSION_NUMBER 2.0
# VERSION_DATE 1998-03-27
# ***************************************************
# SCALE 1.33  1.33   4.0
# ^Z
 1  1  3.03   -2.681  3.615  4.65   -1
 2 -1  2.666  -2.199  6.8    4.646   1
 3 -1  1.674  -0.712  9.876  0.47    2
 4 -1 -0.74    3.842 -0.047  0.47    3
 5  3 -0.253   6.637 -4.4    0.47    4
 6  3 -0.253   7.368 -16     0.47    5
 7  3  0.745   8.592 -18.4   0.47    6
 8  3  1.995   9.337 -20.8   0.47    7
 9  3  3.232   9.829 -1.6    0.47    8
10  3  3.485   9.829 -1.6    0.47    9
11  3  4.482  11.305 -1.6    0.47   10
12  3  4.482  11.544 -1.6    0.47   11
13  3  4.735  13.26  -1.6    0.47   12
14  3  4.735  13.513 -1.6    0.47   13
15  3  4.735  14.005 -2.4    0.47   14
16  3  5.732  14.989 -2.4    0.28   15
17  3  6.224  16.452 -6.8    0.28   16
18  3  6.73   17.689 -10     0.28   17
19  3  8.219  18.673 -11.2   0.28   18
20  3  8.219  18.913 -11.6   0.28   19
21  3  8.219  21.613 -14     0.28   20
22  3  8.219  21.865 -14     0.28   21
23  3  9.47   28.981 -16.4   0.28   22
24  3  9.47   29.233 -16     0.28   23
25  3  9.47   29.473 -16     0.28   24
```

FIG. 26

```
#Na, Ca(HVA), and Ca(LVA) from JC Magee & D Johnston, J Physiology, 487, 67-90 (1995).
#K(A) & K(DR) from DA Hoffman, JC Magee, CM Colbert & D Johnston, Nature, 387, 869-875 (1997).
#K(I) from JC Magee, J Neuroscience, 18(19), 7613-7624.
#K(C) from JC Johnston, DA Hoffman, JC Magee, NP Poolos, S Watanabe, EM Colbert, & M Migliore, J Physiology,
#525, 75-81 (2000).
#Summarized by Mainen & Sejnowski, Methods in Neuronal Modeling, MIT Press (1998).
#distances in microns from midpoint of soma to center of segment.
#channel densities in S/m^2 (=pS/micron^2)
#                                        densities:
cell_type   segment_type  distance_from_soma   Na    Ca(HVA)  Ca(LVA)  K(A)   K(AHP)  K(C)   K(DR)   K(I)
CA1         ax            0                    60    -1       -1       -1     -1      -1     23      -1
CA1         so            0                    60    27       5        25     -1      -1     23      1.5
CA1         ap            0                    60    27       10       25     -1      -1     23      1.5
CA1         ap            70                   i     15       i        i      -1      i      i       i
CA1         ap            105                  i     i        i        i      -1      0      i       i
CA1         ap            350                  60    15       10       123    -1      0      23      9
CA1         bs            0                    20    27       10       25     -1      -1     17      1.5
CA1         bs            100                  20    27       10       25     -1      0      17      1.5

#The following are from RD Traub, JGR Jefferys, R Miles, MA Whittington & K Toth, J Physiology, 481, 79-95 (1994);
#CA3 compartmental model.
TR3         ax            0                    5000  0        0        0      0       0      2500    0
TR3         so            0                    1000  10       0        5      8       200    1350    0
TR3         ap            22                   30    10       0        5      8       80     200     0
TR3         ap            66                   30    10       0        5      8       80     200     0
TR3         ap            103.5                0     20       0        0      8       40     0       0
TR3         ap            141                  0     30       0        0      8       120    0       0
TR3         ap            191                  0     30       0        0      8       120    0       0
TR3         ap            247                  0     10       0        0      8       40     0       0
TR3         ap            325                  0     10       0        0      8       40     0       0
TR3         bs            13                   10    10       0        5      8       80     15      0
TR3         bs            56                   0     10       0        5      8       40     0       0
TR3         bs            113                  0     10       0        0      8       40     0       0

#The following are from RD Traub and R Miles, J Comp Neurosci, 2, 291-298 (1995); interneuron (basket cell)
#compartmental model.
TRi         ax            47.5                 500   0        0        0      .01     0      250     0
TRi         so            0                    500   0        0        0      .01     0      250     0
TRi         ap            35                   25    1        0        .5     .01     8      25      0
TRi         ap            85                   25    1        0        .5     .01     8      25      0
TRi         ap            135                  50    1        0        0      .01     4      50      0
TRi         ap            185                  25    1        0        0      .01     4      25      0
TRi         ap            235                  0     1        0        0      .01     4      0       0
TRi         ap            285                  0     1        0        0      .01     4      0       0
TRi         ap            335                  0     1        0        0      .01     4      0       0

#Na and K conductance densities for O-A interneuron are given in M Martina, I Vida & P Jonas, Science, 287, 295-
#300 (2000); entire TEA-resistant current taken to be K(A), TEA-sensitive divided equally between K(DR) &
#K(C). L Zhang & CJ McBain (J Physiology, 488.3, 661-672 (1995)) say K(AHP) also likely present, but
#conductance density not studied.
OAi         ax            0                    -1    -1       -1       -1     -1      -1     -1      -1
OAi         so            0                    113   -1       0        121    -1      117.5  117.5   0
OAi         ap            100                  113   -1       0        158.5  -1      99     99      0
OAi         bs            100                  113   -1       0        158.5  -1      99     99      0
```

FIG. 27

METHODS AND SYSTEMS FOR DRUG SCREENING AND COMPUTATIONAL MODELING BASED ON BIOLOGICALLY REALISTIC NEURONS

RELATED APPLICATIONS

Under 35 USC 119, this application claims the benefit of the priority date of U.S. provisional application 60/736,599, filed on Nov. 14, 2005, the contents of which are herein incorporated by reference.

FIELD OF THE INVENTION

This invention relates to methods and systems for screening potential medications and compositions using biologically realistic computational network models. The computational network model can be used as a modern drug discovery tool for a variety of medical disorders.

BACKGROUND OF THE INVENTION

The human brain is made up of neurons connected to one another in a complex network. It is believed that when humans learn, new connections are made or existing ones are modified. Neural networks, used in artificial intelligence (A.I.) applications, are massively parallel computing models inspired by the human brain. Such networks are typically implemented by multiple processors connected by adaptive weights. Computational neural models based on such neural networks can simulate brain conditions and provide valuable information and insight about the human brain.

Doctors who treat patients having neuropsychiatric disorders often rely on psychiatric drugs. Specific treatments and drugs exist for specific diagnostic categories of patients. For example, neuroleptics are prescribed for schizophrenia, antidepressants are administered for depression, anxiolytics for anxiety, lithium for mania, and stimulants, such as RITALIN®, for attention-deficit/hyperactivity disorder (ADHA).

Before prescribing drugs to humans, it is prudent to first test them to ensure that they are effective, or at the very least, that they are safe. The most straightforward way to test such drugs is to test them on humans. As late as the middle of the last century, for example, it was routine to test drugs on prisoners and on patients in mental asylums. In fact, the well-known antipsychotic drug chlorpromazine was discovered in this way.

Since then, testing new drugs in this way has been acknowledged as unethical. As a result, the safety and efficacy of new drugs is assessed by testing them on animal models. In the case of psychiatric drugs, this generally involves isolating an animal behavior that is thought to be analogous to a human behavior or psychiatric condition, administering the drug in question to the animal, and observing if the behavior changes. As an example, the operant conflict test in rate is thought to embody behavior analogous to anxiety in humans and the medication DIAZEPAM®, also known as VALIUM®, was discovered by its ability to decrease such behavior in rats in a laboratory environment.

However, not all psychiatric disorders and neuropsychiatric conditions have clear behavioral correlates in animals. For certain neuropsychiatric brain disorders, such as schizophrenia, it is difficult to test the efficacy of a potential drug preclinically, in part because there are presently no well-established animal models of schizophrenia. As a result, using animal models to screen antipsychotic medications for antischizophrenic potency is not feasible. Thus, for many neurologican disorders, there are currently no well-understood and established methods for preclinically screening potential drugs safely and expeditiously.

SUMMARY

The invention features screening test compistitions for their efficacy in the treatment of various types of medical, e.g., neural disorders prior to human clinical trials. Such neural disorders can include, for example, brain disorders manifested as psychiatric disorders, or other disorders, for example disorders of motor function, that are susceptible to neurocomputational modeling.

In one aspect, the invention includes a method for screening a test composition for potential efficacy in treatment of a disorder (e.g., schizophernia). The method includes creating a first computer model (e.g., an "attractor" neural network model) representative of a volume of disease-afflicted neural tissue (e.g., hippocampus) exposed to the test composition. The first computer model includes interconnected neurons, in each of which the quantitatively simulates spatialiy compartmentalized ion channel conductance and receptor actvity. An initiai excitation (e.g., a biologically realistic one) is then provided to the first computer model, and an outcome is then determined. This first outcome is indicative of a response of the first computer model to the initial excitation, which also represents the potential efficacy of the test composition for treating the disorder.

The method can include modeling neurons having an anatomically realistic dendritic arborization (e.g., based on anatomical data from actual cells). The method can also include modeling neurons that have varying ion channel and receptor distributions along the dendro-somatic axis (e.g., based on experimental data for ion channel or receptor distribution). The first computer model can also simulate changes in second messenger concentrations according to the varying distributions of ion channels and receptors. In addition, the first computer model can also simulate the presence ion channel or receptor antagonists. Likewise, the model can also simulate the presence of ion channel or receptor antagonists. In one embodiment, the model imports data from a database (e.g., data for: dendritic arborizations, ion channel distribution, receptor distribution, ion channel antagonists, ion channel agonists, receptor antagonists, or receptor agonists).

One practice of the invention includes creating a second computer model representative of the volume of disease-afflicted neural tissue. This volume is not exposed to the test composition. An initial excitation is then applied to this second computer model to produce a second outcome indicative of a response of the second computer model to the initial excitation. A difference between the first and second outcomes indicates that the test composition is a candidate composition for treating the disorder.

In another practice of the invention, a third computer model representing a volume of neural tissue free of the disease is created and provided with an initial excitation to produce a third outcome indicative of a response of the third computer model to the initial excitation. A similarity between the first and third outcomes indicates that the test composition is a candidate composition for treating the disorder. In one embodiment, a comparison between the outcomes of a first and third model includes determining a first epoch frequency associated with the first outcome, determining a test epoch frequency associated with the first outcome, outcomes, and classifying the test composition as a candidate composition for treating the disorder when the first epoch frequency is associated with the third outcome. (The test composition is also classified as a candidate for treating the disorder when the first epoch frequency is greater than the test epoch frequency and the test epoch frequency is associated with the second outcome.

In yet another practice of the invention, creating a first computer model of the disorder (e.g., a neuropsychiatric or neurological disorder) includes defining a model of a volume of neural tissue (e.g., defining a neural network), the model having a population profile of biologically realistic neurons. The model is then altered to simulate lesioning caused by the disorder (e.g., by altering the population profile to be consistent with the disorder) as well as to simulate the effect of the test compisition on the neural tissue. In one embodiment, interneuron density is reduced in the first computer model, to alter the population profile to be consistent with the disorder.

In another aspect, the invention includes a method for generating a first computer model for determining whether a test composition is a candidate drug for treating a disorder (e.g., a neuropsychiatric or neurological disorder). Generating the first computer model includes generating a computational network model of a normal human brain manifesting a plurality of normal characteristics of human behavior, and introducing a digital representation of one or more physiological lesions into the normal computational network model. The physiological lesions are selected to be consistent with the suspected neuropathology of the disorder. The method further includes applying pharmacological data of the test composition to the computational network, and based on the application of the pharmacological data determining the efficacy of the test composition for treating the disorder. A favorable outcome in the network model indicates that the test composition is a candidate drug to treat the disorder. As used herein, "favorable" means that the computer simulation, i.e., the computational model of the brain disorder, shows signs of physiological improvement consistent with improvements in the brain disorder.

In another aspect of the invention, creating a computer model includes creating a first computational network model for the disorder (e.g., a neuropsychiatric or neurological disorder) and applying input data of a test composition to the first network model to obtain the resulting data. The resulting data from the first network model are then compared with resulting data from a second network model simulating exposure to a composition known to be effective for treating the disorder. The efficacy of the test composition is then determined based on the comparison between the resulting data from the first and second model networks.

In one embodiment, generating the computational network model for the disorder includes generating a model that manifests a plurality of normal characteristics of human behavior, and then introducing one or more physiological lesions to the normal computational network model consistent with suspected neuropathy of the disorder. In another embodiment, applying input data of the test composition includes simulating dopamine induced effects on the computational network model.

Various aspects of the invention can include one or more of the following features. For example, functional characteristics can be added to the comnputational network model to generate a model of the medical disorder by degrading neurons of the computational network model in a manner analogous to that which occurs in humans afflicted with the neuropsychiatric or neurological disorder. The method can also include determining the efficacy of the test composition for treatment of the disorder includes determining whether the application of the test composition modifies behaviors attributable to the disorder in a beneficial way. Applying the pharmacological data of the test composition can include modeling effects of the test composition on dendritic input integrating for producing an axonal output, or affecting neurotransmitter release properties of neurons in the computational network model. The medical disorder can be selected to be schizophrenia, Alzeheimer's disease, dementia, or a seizure disorder.

In another aspect, the invention includes a system for screening a test composition. The system includes a processor and a memory coupled to the processor. Encoded in the memory is software that, when executed, causes the processor to generate a computational network model including biologically realistic neurons, and manifesting a neuropsychiatric or neurological disorder, to apply pharmacological data of the test composition to the computational network model; and to determine, based on the application of the physiological data to the network model of the neuropsychiatric or neurological disorder, the efficacy of the test composition for treatment of the disorder. The biologically realistic neurons of the model can feature one or more of: anatomically realistic dendritic arborizations (e.g., based on anatomical data from actual cells), spatially compartmentalized ion channel conductances, spatially compartmentalized changes in second messenger concentrations, ion channel or receptor distributions that vary along the dendrosomaticaxonal axis. In one embodiment, the system imports data into the model from a database.

In one aspect of the invention, the software when executed, causes the processor to generate a computational network model manifesting a number of normal characteristics of human behavior. The software also causes the processor to introduce structural or functional lesions to the normal computational network consistent with suspected neuropathology of the neuropsychiatric or neurological disorder. For example, the software can cause the processor to add functional characteristics to generate a model of the medical disorder by degrading neurons of the computational network model in a manner analogous to the dysfunction of neurons in humans afflicted with the disorder. In yet another embodiment, the software causes the processor to apply the pharmacological data of the test composition on ion channels.

As an example of the above, the invention can include a computer-readable medium on which is encoded a data structure representative of a biologically-realistic model of a volume of hippocampal tissue. The data structure includes data representative of population of biologically realistic neurons in each layer of the hippocampus, data representative of types of neurons in each layer of the hippocampus; and data representative of synaptic connections between neurons in the hippocampus.

In yet another aspect, the invention includes a method for determining the potential efficacy of a test composition for treating a neuoral disorder. The method includes creating a first computer model representatice of a disease-afflicted neuron exposed to the test composition, in which the model quantitatively simulates spatially compartmentalized conductance of number of ion channels and receptors, as well as the effect of the test composition on the conductance of the ion channels. The model is then provided with an initial excitation, and a first outcome is determined, which is indicatice of the response of the first computer model to the initial excitation. The first outcome is representative of the ability of the composition to treat the neural disorder.

In one practice of the invention, the method includes creating a second computer model representative of the disease-afflicted neuron isolated from the test composition. The second computer model is then provided with an initial exitation, and a second outcome is determined, which is indicatice of a response of the second computer model to the initial excitation. A difference between the outcome of the first computer model and the outcome of the second computer model to an initial excitation, indicates that the test composition is a candidate drug for treating the disorder.

In another practice of the invention, the method includes creating a third computer model representatice of a neuron free of the disease. The third computer model is then provided with an initial excitation to produce a third outcome indicative of a response of the third computer model to the initial excitation. A similarity between the first and third outcomes indicates that the test composition is a candidate composition for treating the disorder.

In various embodiments, the method for determining the potential efficacy of a test composition for treating a neural disorder can include one or more of the following features. For example, creating a first or second computer model of a neuron can include simulating: ion channel or receptor distributions that vary along the dendro-somaticaxis based on experimental data, anatomically realistic dendritic arborizations (e.g., based on data from actual cells), changes in second messenger concentrations, and the presence of an ion channel antagonist, ion channel agonist, receptor antagonist, or receptor agonist. In one embodiment, the method includes importing data into the model from the database.

The invention provides several advantages.

The computational network modeling based on neural networks for drug screening provides rapid screening of chemical compositions in silico for various psychiatric and neurological disorders, even where no suitable animal models exist.

The present computational network modeling systems and methods can be used, for example, by pharmaceutical and biotechnology companies, as part of a comprehensive drug discovery and development process, as well as by academic and other laboratories studying different pharmacological aspects of neuropsychiatric drugs. The new systems and methods of the present invention can be used, alone or in combination with existing methods, to improve the accuracy of the drug screening process in the screening of drug compositions prior to clinical trials. As a result, drug compositions with a likelihood of clinical effectiveness can be readily and quickly identified. This would increase the number of drugs, medications, and agents screened while at the same time decreasing the overall costs of the screening process. Further, drugs and medications that are more effective than currently available drugs can be made safely available for treatment.

The computational network models also provide the ability to model multiple pathways or multiple molecular targets in a single assay. Additionally, the computational models provide the ability to assess test compositions based on their effects on electrophysiology, not just biochemistry, both at the singe cell and network level.

Unless otherwise defined, all technical and scientific terms used herein have the same meaning as commonly understood by one of ordinary skill in the art to wich this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 26 shows the first 25 lines (and header) from a file in the ".swc" format, which specifies dendritic morphology of an actual neuron.

FIG. 27 is a printout of the file "chan_dens," which lists in tabular form the densities of various species of ion channels as a function of distance from the soma.

DETAILED DESCRIPTION

The new drug screening computational network model enables the identification of compositions having desired pharmacological effects on medical disorders. The methods and systems provide valuable infomation and research and development support for pharmaceutical and other companies by enabling sreening of test compositions in silico for medical disorders, including those lacking adequate animal models. Therefore, the new methods and systems provide an adjunct to high-throughput screening (HTS) methods and other tools of modern drug discovery for various types of medical disorders, e.g., neuropsychiatric disorders such as schizophrenia.

First, the overall systems and methods of screening test compositons are described. In later sections, the details of individual steps and elements of the new systems and methods are presented. Then, representative examples are set forth.

General Methodology

The new methods and systems include modeling, on a computer, the effects that different chemical compositions (e.g., drugs) or biological factos have on specific neural disrders. Whan applied to disorders for which no appropriate animal model exists, the new methods and systems of computer-based drug modeling can identify the molecules with a greater likelihood of being efficacious. The method can be used alone, or in conjunction with medical chemistry approaches, rational drug design, in silico computer-aided drug design, or HTS methods.

For example, in the case of disrders for whicfh a computational model can be constructed, medication effects can be applied at the level of single cells. This is generally done by sifting the model parameters that control the neurophysiologic behavior of the model's constituent neurons. Such model parameters can include those representing ion channel conductance or synaptic response proterties. The effects of these changes on the overall behavior of the network can then be observed. The computational network model thus translates the effects of a drug on individual neurons into the effects of the drug on a biological system made up of many neurons.

In its most general sense, a computational network model includes a number of interconnected neurons whose emergent, collective behavior is intended to emulate that of a biological system. The network cellular level parameters present in a network model and measured in a biological system can be of any type. Neural models range in complexity from simple "computational units" that sum a weighted vector of inputs to produce and output, to complex compartmental models that take into account time-varying conductances and Hodgkins-Huxley ion channels. In no case are all underlying neurobiological variables and mechanisms known. Consequently, it is often necessary to begin with a hypothesis to explain an unknown mechanism. This hypothesis is then refined as more experimental data becomes available.

Figure 1:
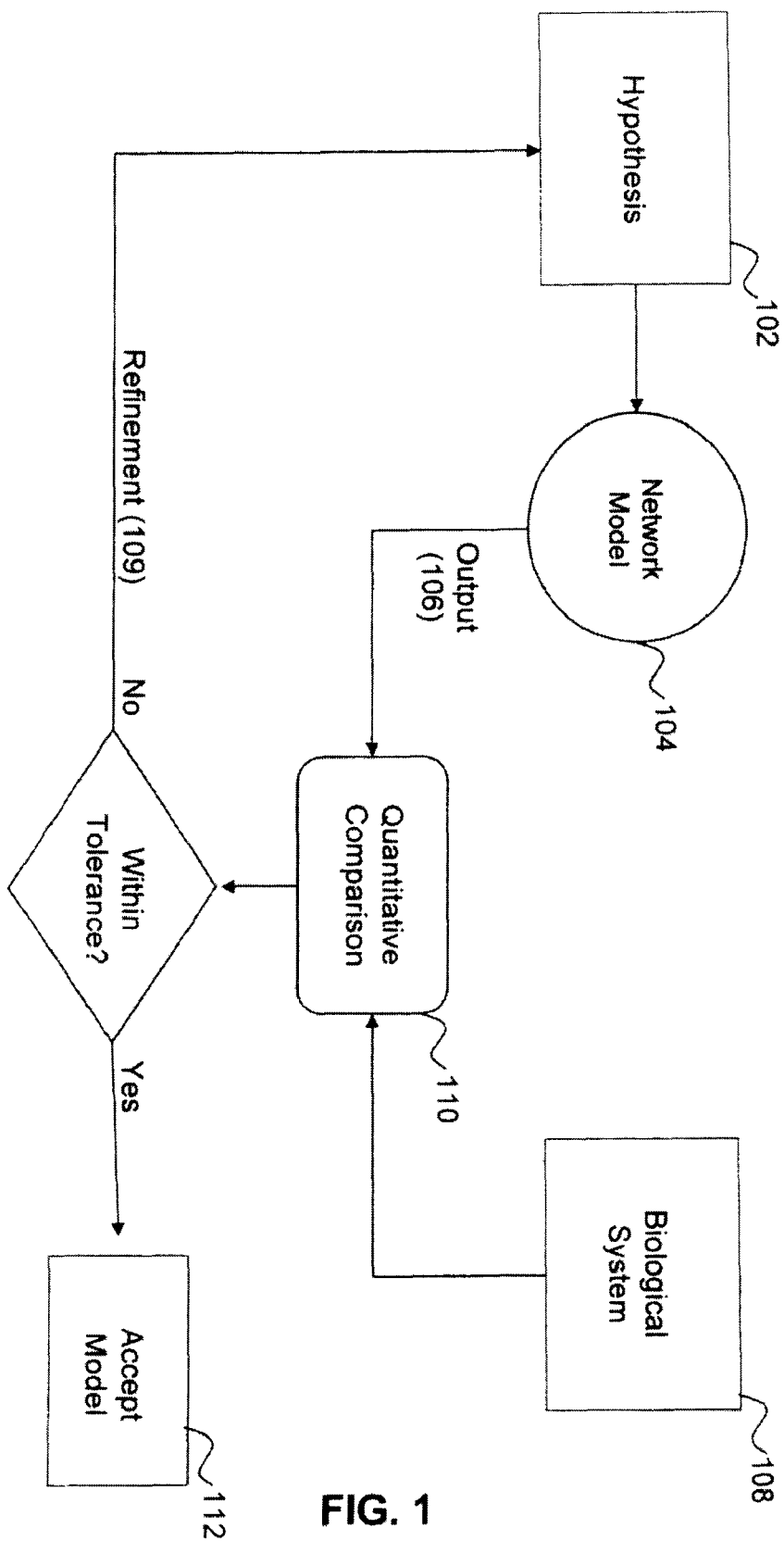
FIG. 1 is a schematical diagram for developing and testing a computational network model.

The development and testing of a computational model for simulating a biological system is by nature an iterative process. Referring to FIG. 1, that process begins with the formulation of a hypothesis (step 102) and the construction of a network model (step 104) embodying that hypothesis. The assumptions about the behavior of the biological systems that underlie the hypothesis are embodied in the equations and the parameters of the model and generally implemented on a computer.

Execution of the model (step 104) results in an output 106 that attempts to simulate the behavior of a biological system. This output 106 is then quantitatively compared with corresponding experimentally observed values (step 110) obtained from the actual biological system (step 108) to determine how well the output (step 106) matches the corresponding observed values from the biological system. If the difference or mismatch is below some threshold, the model is considered suitable for use in making predictions about the behavior of the biological system (step 112). Otherwise, the parameters of the model parameters (step 104). This process continues until model outputs are within reasonable agreement with experimental values.

Neural Networks

A neural network is a computational network model composed of neurons and connections between these neurons. The strength of each connection can be expressed as a "weight". The activation of a given neuron is based on the activation of the neurons that have connections directed at that neuron and the weights associated with those connections.

Computer based neural network simulation, which was originally inspired by artificial intelligence (A.I.) research, has been used to study human cognition, including psychiatric and neurological mental disorders. Computational network models to study human cognition have been modified to better emulate the dynamic nature of human cognitive processes. Accordingly, neural network models are formulated to capture the emergent properties of assemblies of neurons functioning together. As will be described further below, computational network models can be used to study normal and pathological human brain functions. Therefore, by using neural network simulation, human thought processes can be molded by applying principals governing the dynamic interactions within neural ensembles to gain a better understanding of their gross behavior viewed as a cognitive process.

Attractor Networks

It is believed that thoughts, or cognitions, are represented in the brain as patterns of neural activation. The attractor, or "Hopfield," network formulation embodies the maner in which cognitions may be encoded and recalled at the level of ensembles of neurons. This network formulation is useful, as it describes the manner in which clinically observable phenomeno (e.g., memory tasks) can be operationalized computationally.

An attractor network is generally conceptualized as an array of neurons, with each neuron connected to every other. Each neuron calculates the weighted sum of its inputs and applies a transfer function to determine whether the neuron will be active or inactive. A "memory" consists of a pattern of activation of the consituent neurons. One teaches the network by activating the neurons of a particular memory and then applying a Hebbian learning rule (i.e., interneuronal synaptic connections are not static, but can rather vary in strength, depending on the past activity of the constituent neurons), which adjusts the weighting of the inter-neuronal connections. A well-taught network, when presented with a fragment of a memory, will return the complete, intact memory. The example presented below is implemented using an attractor network.

Attractor networks have three interrelated properties: (1) memories are stored in a content addressable manner, (2) they are represented in a distributed, rather than localized, form; and (3) the systems are capable of generalization. These characteristics capture the essential ways that attractor networks mirror actual neurobiological processes.

In a content-addressable system, the memory does not "exist" in any particular location, but is spread over several processing units. For example, humans are able to recall items from memory based on a partial description of their contents, and can even do so if the description is not entirely correct. In such a system, referred to as a "content addressable system," a fragment of a memory provides access to the complete, stored memory. In contrast to the manner in which computers assign each memory to a particular location, artificial neural networks have the ability to recall complete patterns from fragmentary input stimuli.

In a distributed representation, several neurons are involved in the storage of a given memory, and a particular neuron will often be part of the brain's representation of several distinct memories. In part for this reason, removal of one or a small number of neurons from a neural network does not excise a particular memory, nor does it cause a significant decline in overall performance.

In a generalized system, if a network learns new information about an item, that new information is also applied to similar memories stored in the network. This is because memories are distributed among nodes of the network. Hence, two similar memoreis may have a large number of activated nodes in common; that is, their patterns of activation will overlap.

Figure 2:
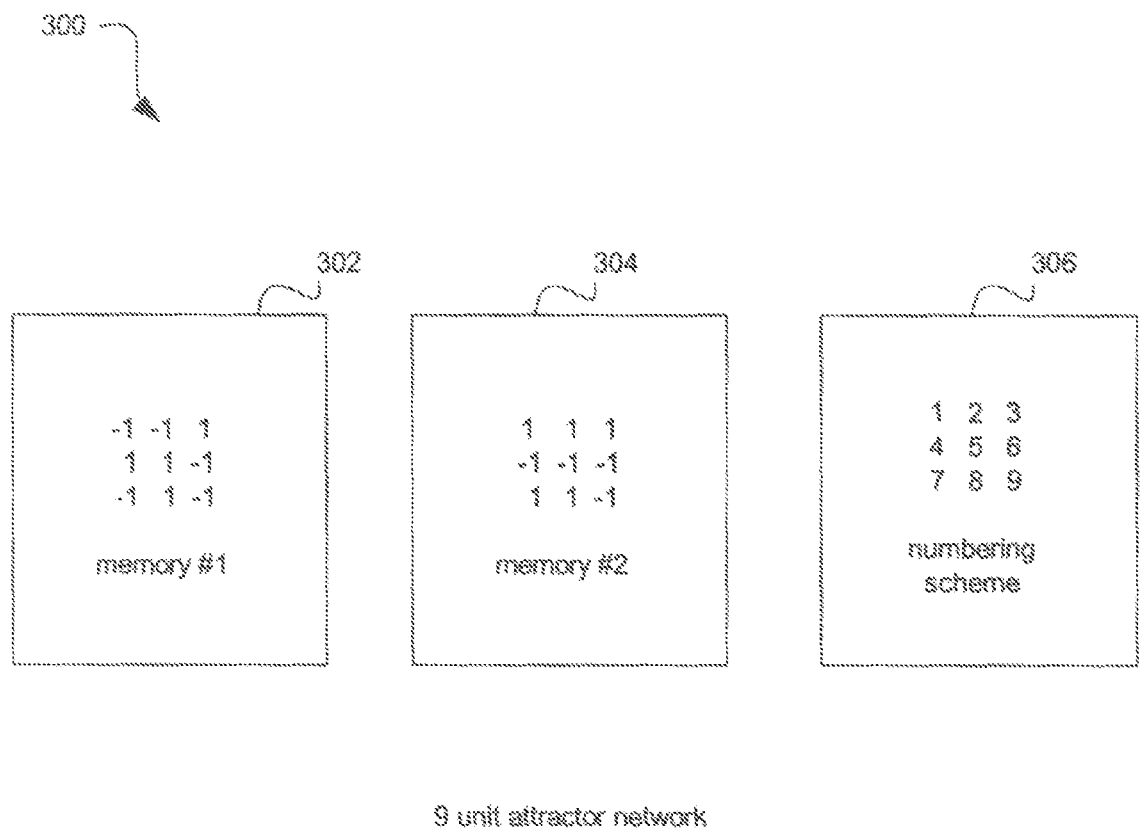
FIG. 2 is a schematic representation of a two-memory state for a nine-unit atractor network.

For example, referring to FIG. 2, in an attractor network 300, nine neurons are arranged in a 3×3 array, with each neuron reciprocally connected to every other. In a given cycle, each neuron adjusts its internal state based on the inputs from the other eight neurons in the network 300. The activation state of each neuron will be designated $\mu_i$. An active neuron is represented as +1 and an inactive neuron as −1. In FIG. 2, two memory states 302 and 304 to be stored are shown.

The synaptic strength of the axonal connection from neuron i to neuron j, designated as $T_{i \rightarrow j}$, measures the effect of neuron i on neuron j. This synaptic strength can be positive (excitatory), negative (inhibitory), or 0 (i.e., no axonal connection). The overall effect on neuron j from all other neurons in the system, designated $S_j$ below, is given by:

$$S_j = \sum_{i=1}^{9} T_{i \rightarrow j} \times \mu_i, \; i \neq j.$$

If this sum positive, the neuron is activated (i.e., set to +1); if it is negative the neuron is rendered inactive (i.e., set to −1). For a given cycle, the activation state of each neuron in the system is calculated in this way.

The first step in implementing an attractor network is to store memories. This is done by examining each pair of neurons in the system. For instance, if, for a given memory, the activation states of two neurons are the same (i.e., +1 and −1 and −1), the synaptic strength between them is increased. If they are different (+1 and −1), the synaptic strength between them is decreased. This is carried out for all neurons, across all memories. Mathematically, with M memories, this can be represented by a weight T:

$$T_{i \rightarrow j} = \sum_{m=1}^{M} \mu_i^m \times \mu_j^m,$$

If two neurons in the system are both active (or both inactive) in several memories, the weight T connecting them is large. Conversely, if the activation levels of two particular neurons are different, the weight T is negative. Once the neural network has been trained, the set of weights associated with the network, i.e., the weight matrix, represents the learning of the network. With the formulation given here, the number of memories a network remembers is approximately 0.15 times the number of neurons in the system.

For memories 302 and 304 of FIG. 2, the inter-neuronal weights for the first few combinations is as follows:

$T_{1-1} = (-1 \times -1) + (1 \times 1) = 2$ $T_{2-1} = (-1 \times -1) + (1 \times 1) = 2$ $T_{3-1} = (1 \times -1) + (1 \times 1) = 0$ $T_{4-1} = (1 \times -1) + (-1 \times 1) = -2$ This calculation is carried out for all 9×9 neuronal connections. The learning rule results in symmetric weights: $T_{1 \rightarrow j} = T_{j \rightarrow 1}$.

To test the performance of a network after learning, a fragment of one of the stored memories is supplied to the network. For example, the top three neurons of a start-up array can match those of memory 302:

−1 −1 1

0 0 0

0 0 0

Next the weighted input to each neuron in the system is computed based on this startup array. For neuron 1, S would be calculated as follows:

$$S_i = (T_{11} \times \mu_1) + (T_{21} \times \mu_2) + (T_{31} \times \mu_3) + \ldots$$
$$= (2 \times -1) + (2 \times -1) + (0 \times 1) + \ldots$$
$$= -4$$

Performing the above computation for each neuron in the system yields the following set of $S_j$s:

$S_1 \; S_2 \; S_3$ −4 −3 2

$S_4 \; S_5 \; S_6$ =4 4 −2

$S_7 \; S_8 \; S_9$ −4 2 −2

Applying threshold functions (if $S_j$>0, neuron j is on, otherwise, neuron j is off), the following pattern emerges:

−1 −1 1

1 1 −1

−1 1 −1

In attractor networks, an energy function is defined as follows:

$$E = -1/2 \sum_{i=1}^{N} \sum_{j=1}^{N} T_{ij} \mu_i \mu_j$$

Figure 3:
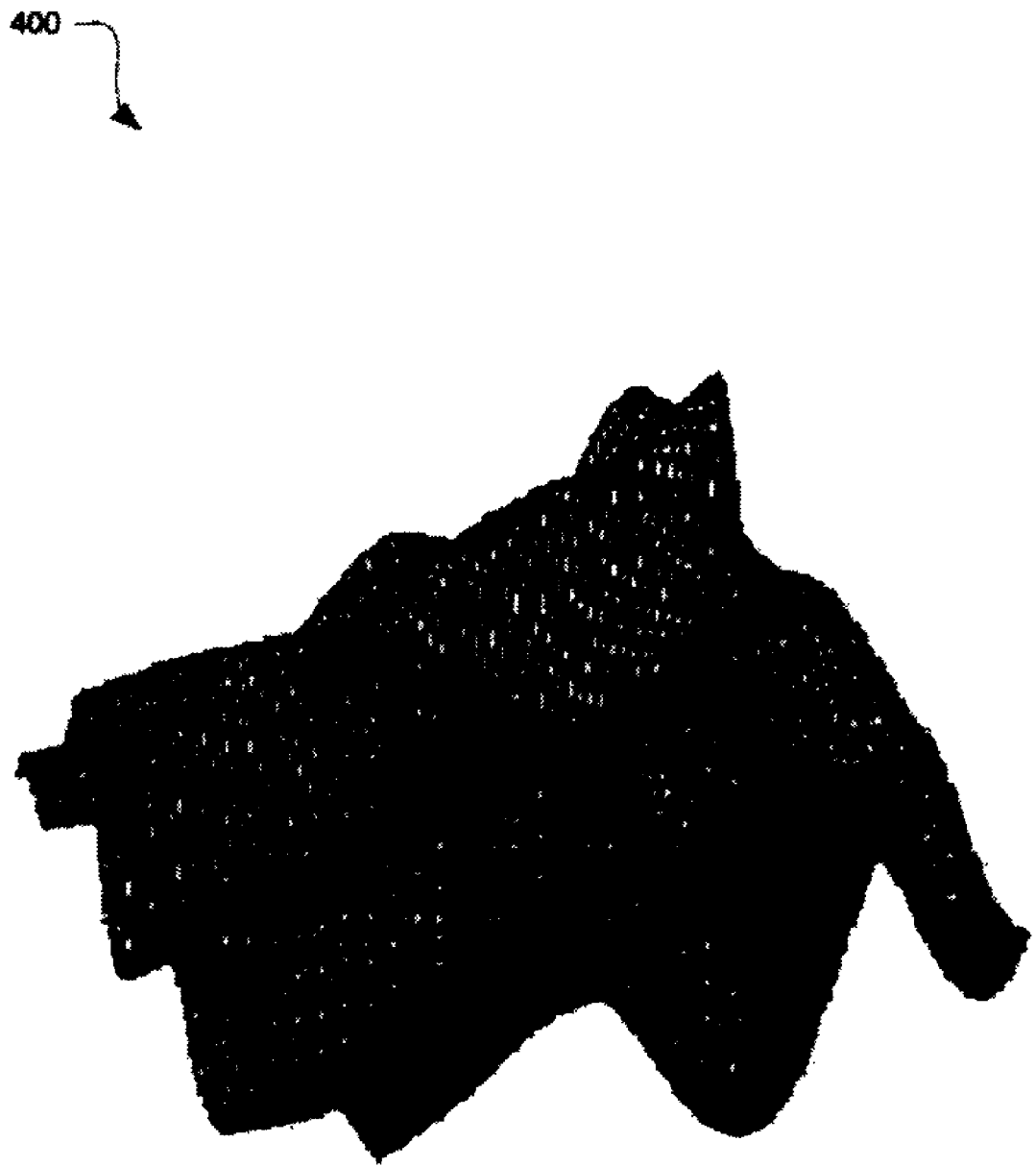
FIG. 3 is a schematic representation of an energy landscape of an attractor network.
Figure 4:
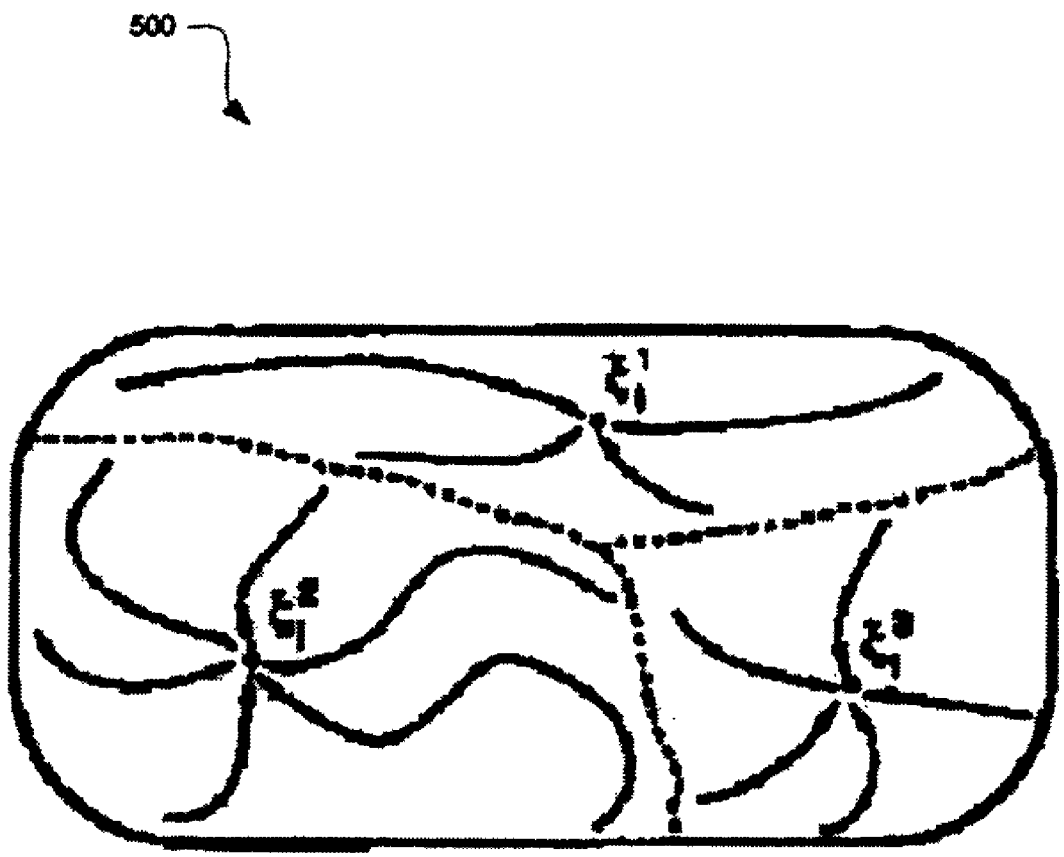
FIG. 4 is a schematic representation of a computational network of an attractor network.

Referring to FIG. 3, the energy function can be viewed as an energy landscape 400 having an energy level (z axis) and a network state-space (the x-y plane). The landscape 400 includes all $2^N$ possible combinations of the network (where N is the number of neurons in the network). Each of the local minima of the network corresponds to a memory. As the network evolves, i.e., as the activation states of its neurons are cyclically updated, the energy decreases. Thus, as the network goes through successive cycles of updating, the state of the network flows down the valleys of the energy function, analogous to a ball rolling down hill. The network eventually stabilizes at one of these local minima, or "attractors." Referring to FIG. 4, a schematic 500 of the state-space of a model with three attractors represents a "projection" of the energy landscape onto the x-y plane. The state-space is divided into "basins of attraction." In a neural network, if the memory cue is within one of these basins, it is drawn to the indicated memory state.

The change in the energy level of the network due to the change in state of a given neuron $\mu_i$ (i.e., from −1 to +1, or from +1 to −1) is given by:

$$\Delta E_i = -1/2 \Delta \mu_i \sum_{j=1}^{N} T_{ij}\mu_j, \quad j \neq i$$

Biologically Realistic Computer Model of a Neuron

To prepare a computational model of a neural tissue sample, on first creates a biologically realistic computational model of a single neuron. As used herein, a biologically realistic model of a neuron is one that explicitly models trans-membrane potentials and time-variations thereof and in addition includes one or more of the following features: biologically faithful dendritic arborizations (e.g., based on digitized data from actual neurons), biologically accurate ion channels and their spatially compartmentalized distributions along the dendro-somaticaxis, ligand-dependent receptors and their spatial density distriutions, dissociation constants ($K_i$) for various ligands that can bind to the receptors (e.g., neurotransmitters and psychoactive drugs), receptor-mediated intracellular signaling through second messenger systems, and spatially compartmentalized quantitative transduction of receptor-mediated events to ion channel conductances. Specific values for these parameters can be obtained from the published literature.

In one implemtation, the various parameter values (e.g., $K_i$) are directly imported into the model from online databases. Using such data sources avoids the need for extensive literature searches to collect the relevant data, and allows a more automated updated of the model as new information becomes available.

Figure 5:
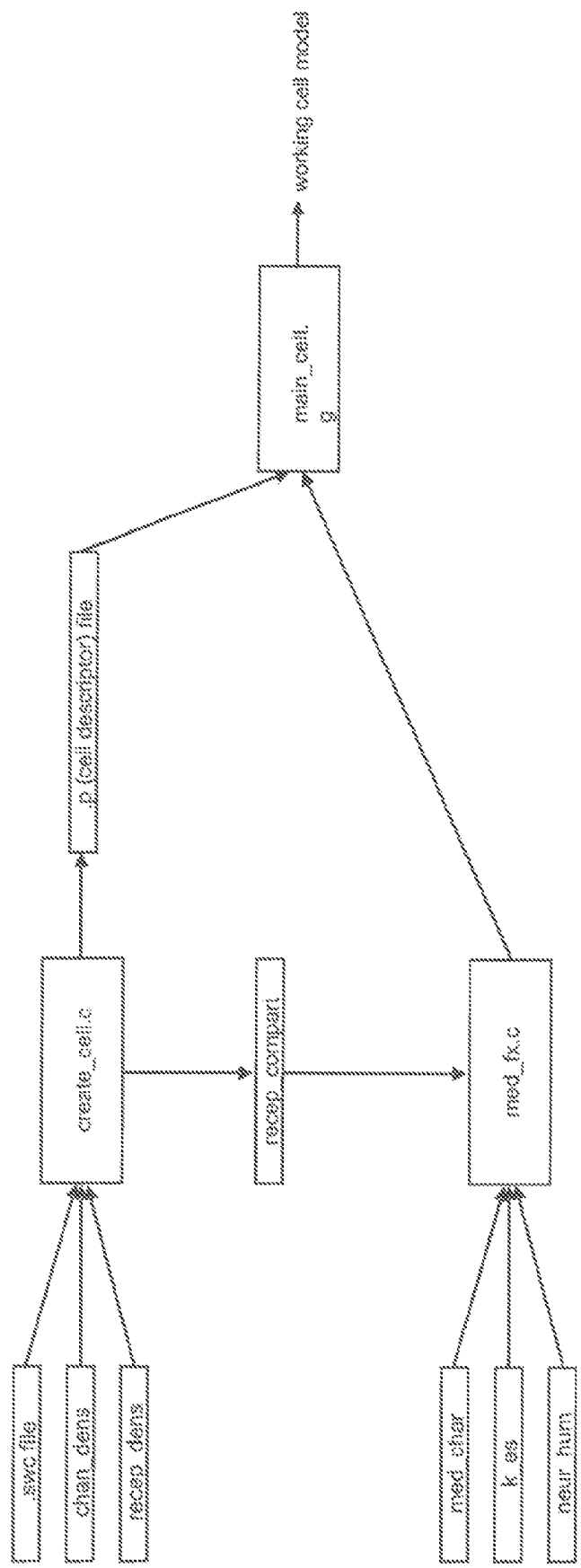
FIG. 5 is a schematic of representation of the process for generating a model of biologically realistic neuron.

A schematic of the overall process for generating a biologically realistic neuron is shown in FIG. 5. Although we have used the GENESIS modeling language, and although we detail the process in terms of this code in an exemplary embodiment, it should be understood that any object-oriented neural modeling language can be used in the disclosed the methods.

Dendritic Morphology

At one time it was assumed that dendrites are simply passive conduits to convey signals to the cell body. More recently, however, it has been seen that dendrites are active structures that can carry out many non-linear tasks (see, e.g., Kich & Segev (2000), Nat. Neurosci 3:1171-1177). For this reason, it is important that a neural model contain a realistic representation of dendritic tress.

In some embodiments, neuronal morphology data can be downloaded from an online database. For example, The Hippocampal Neuronal Morphology Archive (found on teh world wide web at www.compneuro.org/CDROM/nmorph) is an online repository of files containing the dendritic structures of actual cells from various brain areas (hippocampus CA1, CA3, etc). Each file contains a complete description of an actual cell's dendritic tree, specified using x, y, and z coordinates, diameters of dendritic segments, branch points, and codes identifying location of those segments in a cell (apical vs. basal, etc). In one embodiment, these data are downloaded in the .swc format, a publicly available standard developed and documented by MicroBrightField Inc. (Williston, Vt. USA).

Ion Channel Distribution

Figure 6:
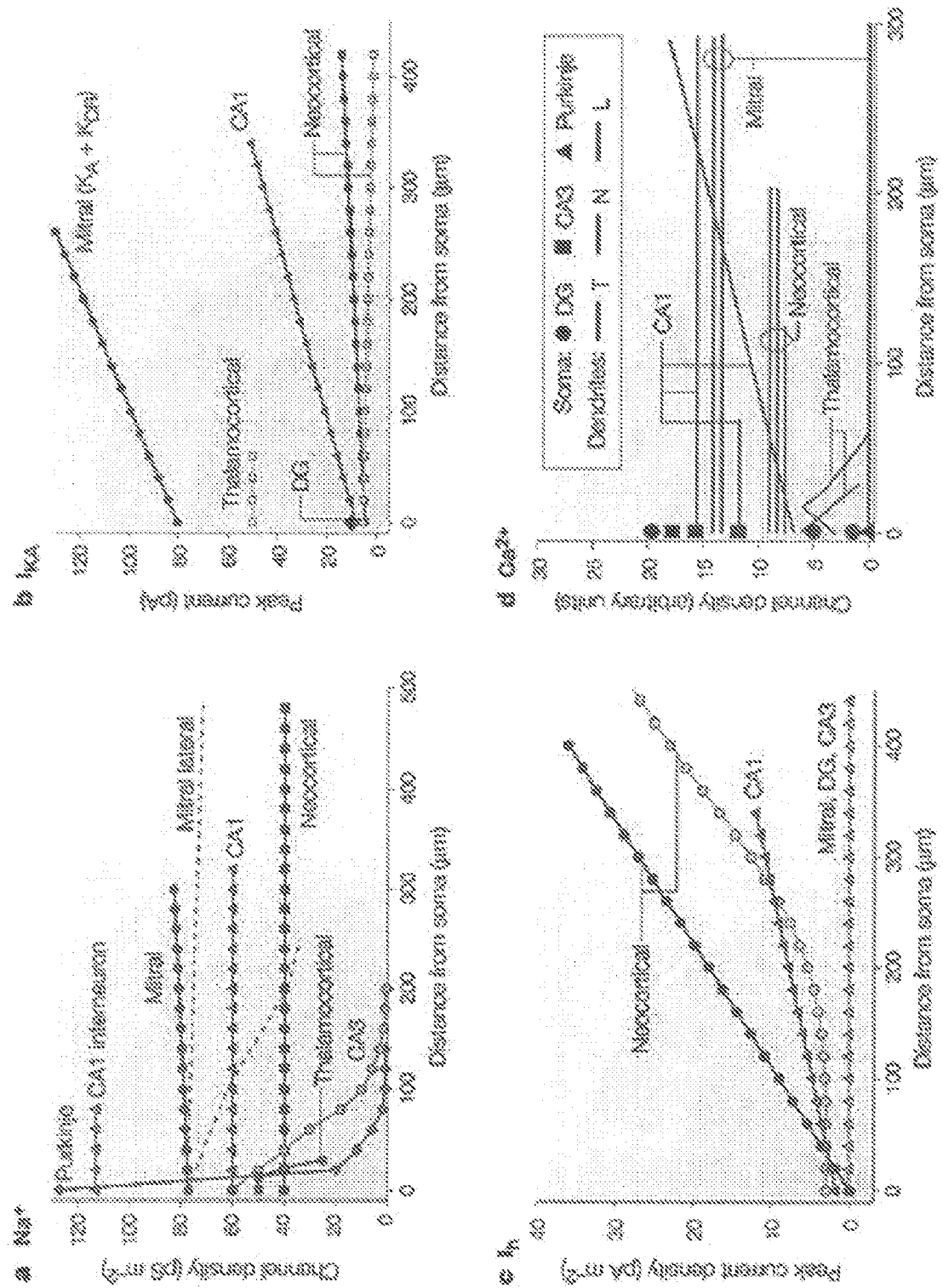
FIG. 6 shows ion channel density data for four different ion channels ($Na^+$, $I_{KA}$, $I_h$, $Ca^{2+}$) for a number of different types of neuron.

There is a growing appreciation that the distribution of various species of ion channels along the dendro-somatic axis is a key determinant of the manner in which neurons process signals. Along with this, there is a significant amount of research producing detailed quantitative data in this area (see, e.g., Migliore and Shepherd (2002), Nat. Rev. Neuroschi., 3:362-370). For example, FIG. 6 shows summary data for four different ion channels ($Na^+$, $I_{KA}$, $I_k$, and $Ca^{2+}$) for a number of different neuron types (hippocampal CA1, CA3, neocortical, etc). Panel (a) shows sodium chanel density as a function of distance from the soma in different neuronal cell types. Panel (b) shows peak potassium current as a function of distance from the soma in different neuronal cell types. Panel (c) shows peak $I_h$ cationic current density as a function of distance from the soma in different neuronal cell types. Panel (d) shows calcium channel density as a function of distance from the soma in different neuronal cell types. As is clear from FIG. 6, the spatial distribution of ion channels and ion channel currents varies dramatically between ion channel types and between neuronal cell types.

Figure 7:
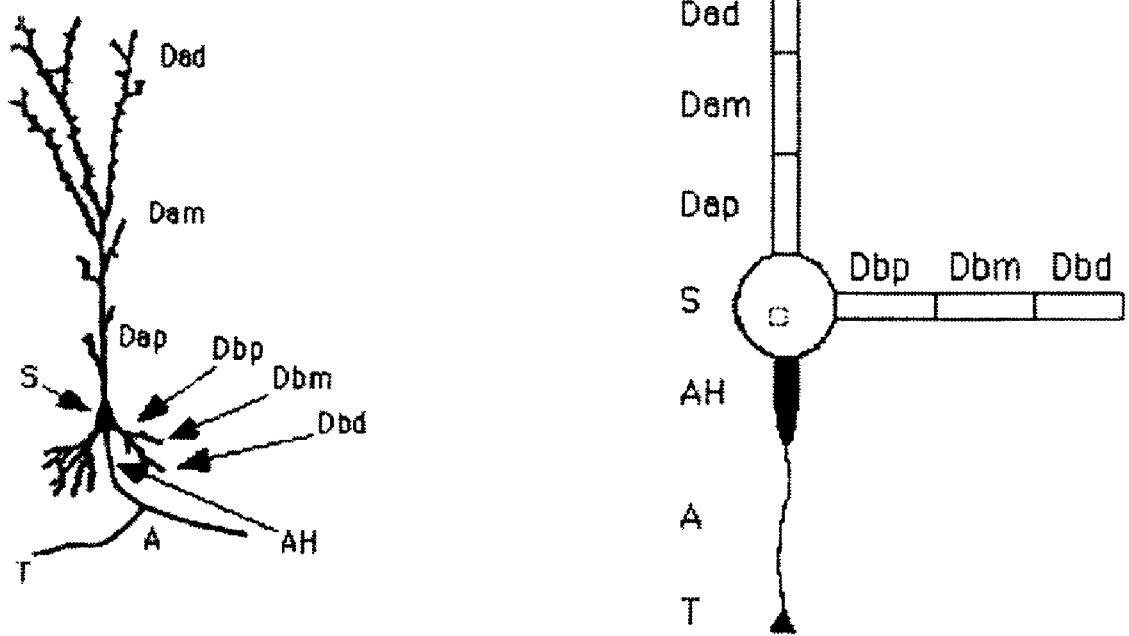
FIG. 7 shows an example of a schematic representation of a cell and its compartments in the NeuronDB database.

In some embodiments, ion channel distribution data can be obtained from an online database. For example, NeuronDB (found on the world wide web at senslab.med.yale.edu/senslab/NeuronDB/default.asp) lists ion channel and receptor densities for a wide variety of different cell types. For a given cell type, a schematic form is given, as shown in FIG. 7. For each particular compartment (e.g., soma, [S], or proximal apical dendrites, [Dap]) ion channel and receptor densities, to the extent known, are given, with commentary and literature references. This information is continuously updated and provided via menu-driven web interfaces; downloadalbe data files are also available. Levels of cell compartments (relative to the soma) are as follows; Dad (distal apical dendrite); Dam (middle apical dendrite); Dap (proximal apical dendrite); S (soma); AH (axon hillock); A (axon); T (axon terminal); Dbd (distal basal dendrite); Dbm (middle basal dendrite); and Dbp (proximal basal dendrite).

Implementation

In one embodiment, a program written in the C programming language results in a creation process that creates a GENESIS single cell model from data files containing information on dendritic morphology and ion channel densities. Specifically, the inputs to this creation program, "makeproto.c," include (1) the aforementioned swc file describing a dendritic arborization pattern, (2) a data file, "chan_dens," listing, in tabular form, densities of all species of ion channels present at discrete points along the dendro-somatic axis, and (3) a data file termed "recep_dens," analogous to the "chan_ dens" data file, that specifies distribution of neuroreceptors along the dendro-somatic axis. In cases lacking specific quantitative information, default values are used. Makeproto.c also outputs a "recep_compart file" that lists the density of each species of neuroreceptor in each of the computational compartments created by the program. Receptor densities are used in calculating medication effects, as described below.

The output of makeproto.c is a "p file," which is in a format specific to GENESIS. GENESIS uses teh p file to create a functioning single-cell model. The p file includes lines that describe corresponding computational compartments of the overall model. It does so by specifying compartment dimensions, connections with other compartments, and channel densities. Details associated with creating a p file are provided in Bower and Beeman (1998).

Figure 8:
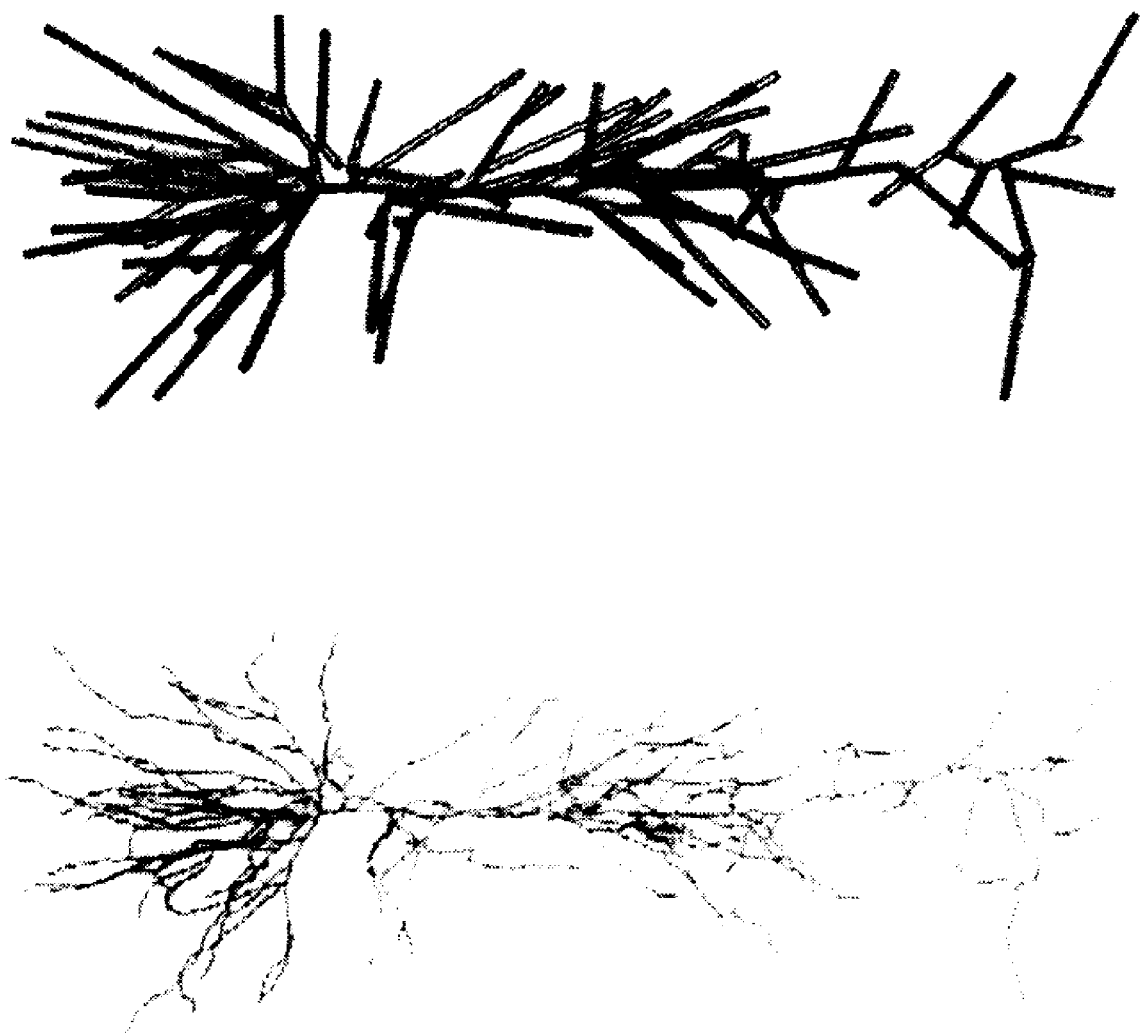
FIG. 8 show a schematic of a biologically realistic neuron created by the program "makeproto.c" (top panel) which is based on a real neuron (bottom panel).

When the makeproto.c program reads the swc file, it ignores all points that are not branch points. It does so by neglecting "kinks" in unbranched dendritic segments. Each segment between branch points is defined as a computational compartment. A schematic of a neuron thus created is shown in FIG. 8, above a drawing of the actual neuron from which it was derived. The makeproto.c program places ion channels in these compartments according to the information contained in the "chan_dens" file. If data is unavailable for a particular region, (i.e., an area of the dendritic tree a particular distance from the soma) ion channel or receptor density values for that region are interpolated between values for the densities of the ion channels and receptors in nearby regions for which they are known.

Intracellular Messaging

Figure 9:
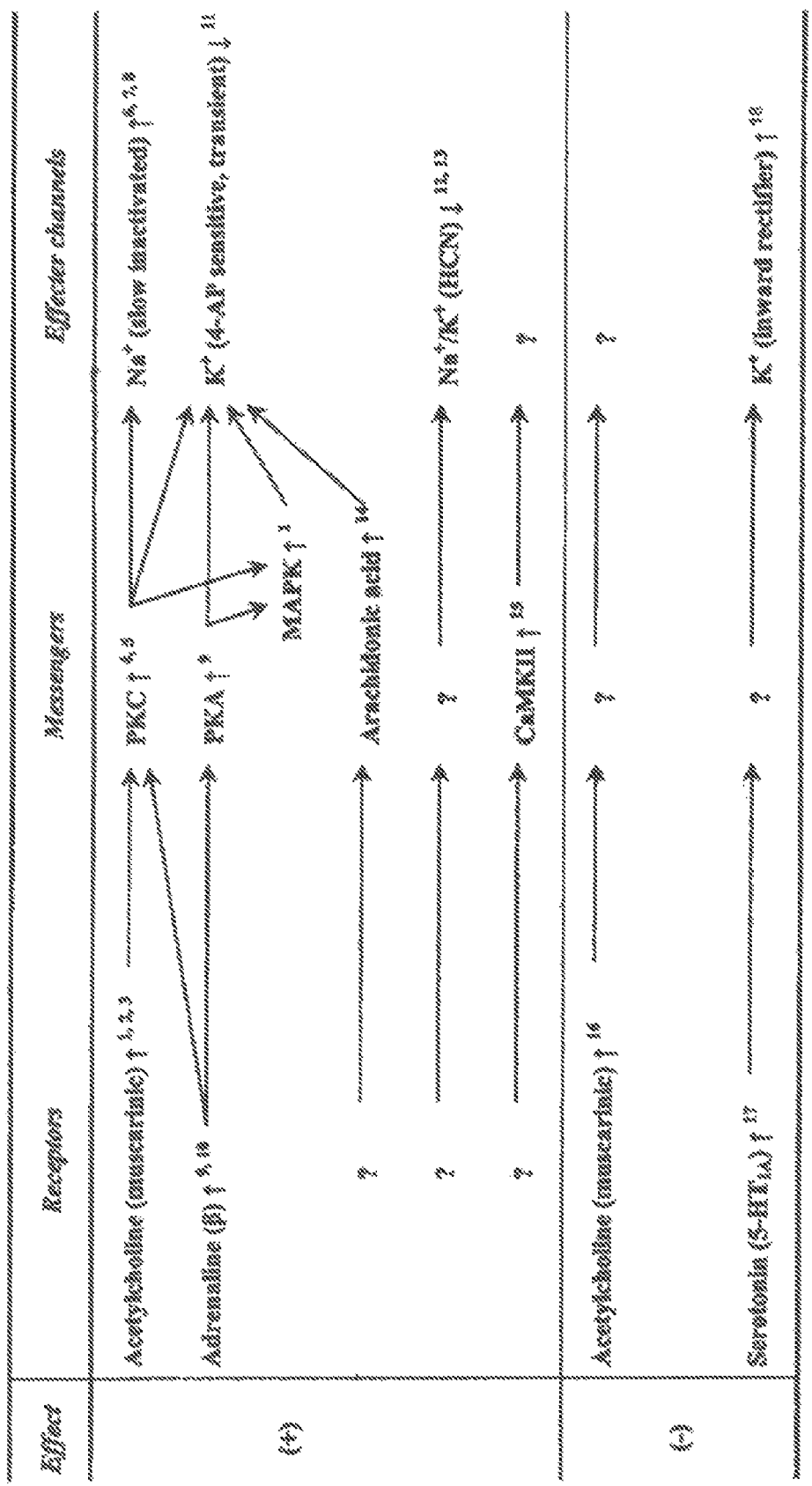
FIG. 9 shows a schematic representation of a network of intracellular interactions which shows examples of receptor→second messenger→ion channel effects in hippocampus CA1 neurons.

In many cases, when a receptor is activated (e.g., by a medication), its ultimate effects on ion channel functioning are mediated by intracellular second messenger pathways. Many sych pathways have been identified, and because they share common elements, there is considerable interaction between them. For this reason, it is difficult to predict the downstream consequences of an upstream ecen (e.g., an increase in cAMP level resulting from activation of a G protein coupled receptor). It is particularly difficult if there are multiple upstream events and significant interplay can occur. An example of such a network of intracellular interactions is shown in FIG. 9, which summarizes receptor→second messenger→ion channel effects in hippocampus CA1 neurons.

Similations of intracellular enzymatic pathways are fairly well developed. Available models generally include terms for the size of the intracellular pools of various reactants, and parameters embodying forward and backward rate constants, which may be under enzymatic control. However, these models have generally not included the far "upstream" effects of drugs at receptors, or "downstream" end effects of second messengers on ion channels.

The database of quantatative cellular signaling (DOQCS) (see Sivakumaran et al. (2003), Bioinformatics, 19(3): 408-415) is an extensive online database providing data representative of signaling cascades for a wide variety of cell types. The database (available on th world wide web at doqcs.ncbs.res.in) includes data descriptive of a large number of second messengers; parameter values (e.g., for reactant pool size and rate constants) drawn from the biological literature are included as part of the site.

In some embodiments of the disclosed methods, data representative of intracellular signaling, parameters, such as that found in DOQCS, is used to model detailed intracellular interactions and their effects on ion channel behaviors. The intracellular signaling data available in DOQCS is particularly convienient since much of it is both comparable with GENESIS and freely downloaded. However, this data includes neither drug-induced receptor effects, nor dynamic alteration of ion channel behaviors as discussed below.

Each element of the biologically realistic neuron model, e.g., a cell compartment, ion channel, or synapse, is encoded as an object. Information from one object is made known to other objects via message passing. Additional information on GENESIS, the object-oriented language used in disclosed methods, can be found in its online manual (available on the world wide web at genesis-sim.org/GENESIS/Hyperdoc/Manual.html.)

Various embodiments of the disclosed methods include creating an object type, termed "convert," that converts a second messenger pool size to a change in an ion channel conductance, FIG. 9, for example, shows that increases in arachidonic acid lead to decreases in $K^+$channel activity. In this example, the size of the arachidonic acid pool (calculated by the GENESIS object of type "pool" [genesis-sim.org/GENESIS/Hyperdoc/Manual-26html#ss26.48]) is communicated to a "convert" object. At each simulation time step, this object calculates the change in the $K^+$ channel conductance from the change in arachidonic acid level. Finally, a message reporting this change is passed to the object representing the $K^+$ channel (e.g., a "tabchannel" object) via message passing.

Receptor-level Medication Effects

For various embodiments of the disclosed methods, one of the primary applications is the translation of medication or neurohumoral effects to changes in cell-level behaviors and their impact on multicellular network activity (e.g., in the CA1 region of the hippocampus). Thus, the pharmacodynamics of drug-receptor interaction at the neuroreceptor level are explicitly included in the disclosed models.

A wealth of data on the pharmacokinetic properties of many psychoactive drugs is available in biomedical literature and, most conveniently, in online data bases. In some embodiments, pharmacokinetic data is imported directly from a website maintained by the Psychoactive Drug Screening Program (PDSD), an NIMH-funded initiative that provides screening of psychoactive composition (available on the world wide web at pdsp.cwru.edu/pdsp.htm). Both pharmacokinetic data (e.g., $K_i$ values) and functional data (e.g., effects on second messenger levels, such as cAMP) are imported into the model, e.g., from an extensive online database of these values (available on the world wide web at pdsp.cwru.edu/pdsp.asp).

Figure 10:
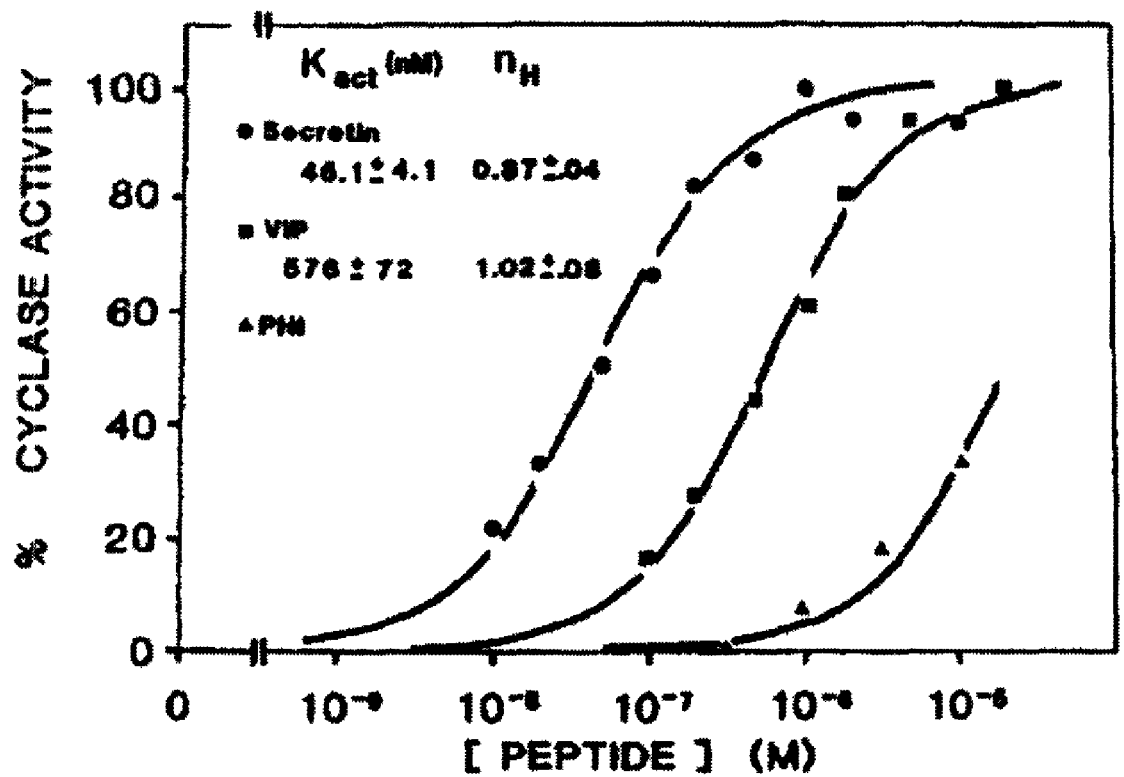
FIG. 10 shows a graphical representation of an example of second messenger biosynthetic enzyme activity as a function of receptor agonist concentration.

Functional data is represented in the disclosed model using the following formal, also used in the PDSP database (available on teh world wide web at kidb.cwru.edu/nimh/function-P.php:

$$V = \frac{V_{max} \times X}{K_{act} + X} + NSA \qquad (1)$$

where V=activity of the intracellular species in question; X=concentration of the composition of interest; $V_{max}$=maximum activity; NSA=non-specific activity at baseline; and $K_{act}$ is a fiting parameter. Graphically, results of functional assays appear as shown in FIG. 10.

Figure 11:
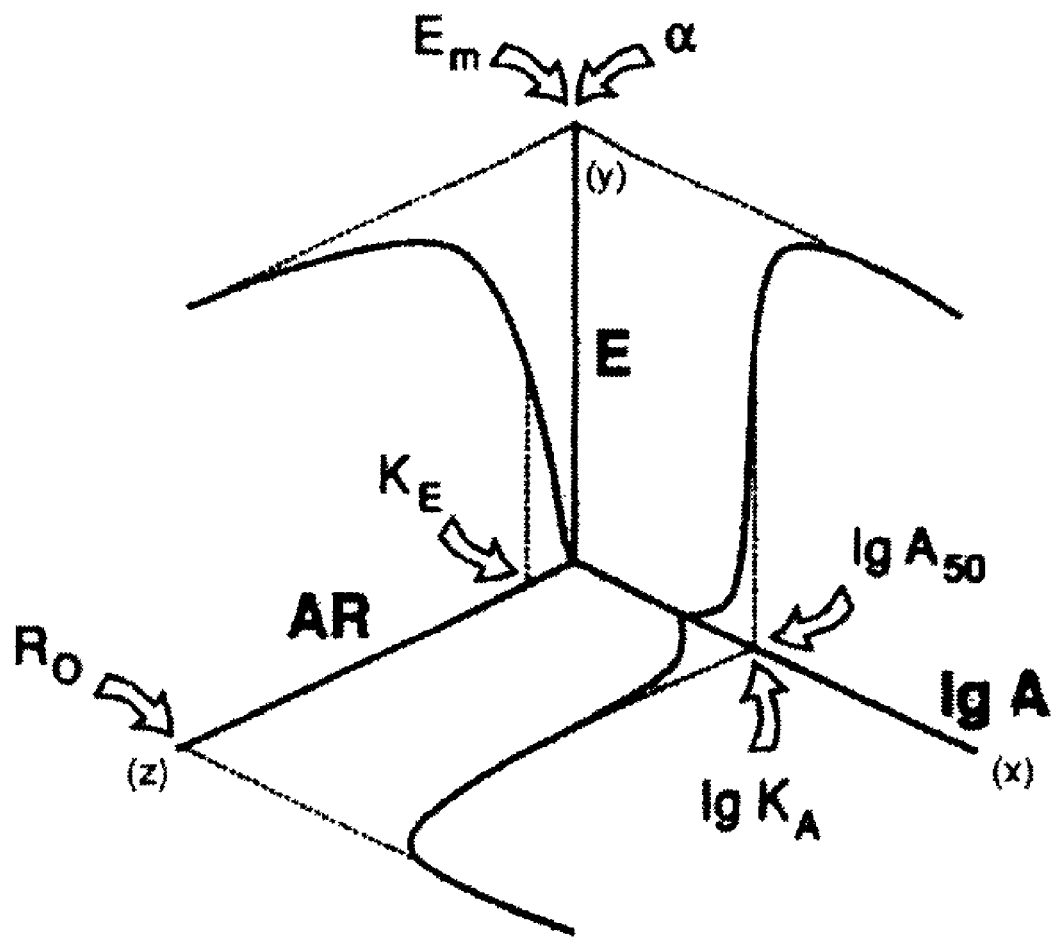
FIG. 11 shows a graphical representation of the operational model of drug action.

In one embodiment, medication effects on the model neuron, are based on the operation model of drug action summarized in FIG. 11. This approach is useful because it conceptually and mathematically separates affinity, represented by $K_A$, and efficacy, as embodied by the term $K_A$. Affinity is the tendency for a given molecule tp bind with a given receptor. (OF note, $K_A$ is identical with the aforementioned $K_i$. We have used $K_A$ in teh following for the sake of consistency with Kenaken (*Pharmacologic Analysis od Drug-Receptor Interaction* (1997), New York: Lippincott-Raven), a standard text.

Agonists.

FIG. 11 indicates the interdependence of agonist concentration, termed "IgA" in teh figure, and response (e.g. a change in level of an intracellular messenger) (XY plane), agonist concentration and formation of agonist-receptor complex, AR (XZ plane), and the relationship between AR and response, E (YZ plane).

In accordance with the operational model, response is assumed to be a hyperbolic function of agonist concentration. That is, the relationship represented in the XY plane can be expressed as:

$$E_o = \frac{[A]E_m}{[A]+b} \quad (2)$$

where $E_a$ is response, $E_m$ is maximal response, [A] is agonist concentration, and b is a fitting constant.

The relationsip between agonist concentration and the quantity of agonist-receptor complex, [A·R], (XZ plane) is given by $$\frac{[A \cdot R]}{[R_t]} = \frac{[A]}{[A]+K_A} \quad (3)$$

Where $R_1$ is receptor concentration, and $K_A$ is the equilibrium dissociation constant; this is the familiar Langmuir adsorption isotherm.

Combining Equations 2 and 3, and assuming $K_A > b$, the relationship shown in the YZ plane can be expressed $$\frac{E_a}{E_m} = \frac{[A \cdot R]}{K_E + [A \cdot R]}, \quad (4)$$

$K_E$ can be calculated using $$[A_{50}] = \frac{K_A}{1+([R_t]/K_E)} \quad (5)$$

where $A_{50}$ is the concentration of agonist that produces half maximal response, and can be calculated using Equation 2.

Combining Equation 4 and Equation 3 yields the following $$\frac{E_a}{E_m} = \frac{[R_t][A]}{K_A K_E + ([R_t]+K_E)[A]}. \quad (6)$$

This is the central equation of the operational model, as it defines production of cell-level response in terms of agonist concentration, affinity of agonist for receptor, and efficacy.

Antagonists

Competitive antagonists funtion by binding to receptors. They do not, by themselves, elicit a downstream response. Instead, they decrease the stimulation that agonists can deliver to the cell. Specifically, in the presence of an antagonist with concentration [B] and dissociation constant $K_B$, the fractional receptor occupancy by an agonist A is given by the following equation:

$$\frac{[A \cdot R]}{[R_t]} = \frac{[A]}{[A]+K_A(1+[B]/K_B)} \quad (7)$$

Clearly, if a receptor is not being stimulated (by another medication or a neurotransmitter in the neurohumoral milieu) a competitive antagonist will have no effect.

In one embodiment, a medication effects program is encoded in the computer language C. The output of this program is GENISIS code that is read by main_cell.g, which is the program that defines and executes the overall cell model.

The three input files to the medication effets program are the medication characteristics file, the efficacy values file, and the neurohumoral milieu file (see FIG. 5).

Medication Characteristics

This medication characteristics input file specifies, in quantitative terms, the agent to be screened or evaluated. The format of this file is as follows.

| Line 1: | concentration of agent | | | | |
|---|---|---|---|---|---|
| Line 2: | D1 | D2 | α1 | α2 | β1 ... |
| Line 3: | $K_A$ | $K_A$ | $K_A$ | $K_A$ | $K_A$ ... |
| Line 4: | cAMP | . | . | . | . |
| Line 5: | $V_{max}$ | | | | |
| Line 6: | $K_{act}$ | | | | |
| Line 7 | NSA | | | | |
| Line 8 | PI (phosphoinositol) | | | | |
| Line 9 | $V_{max}$ | | | | |
| Line 10 | $K_{act}$ | | | | |
| Line 11 | NSA | | | | |
| . | . | | | | |
| . | . | | | | |
| . | . | | | | |

Entries in bold are headings, those in normal typeface represent the actual data values.

Included in line 2 are all receptors at which a given agent acts. Line 3 gives the equilibrium dissociation constant of the agent at each receptor; by convention, positive values are used for agonists and negative values for antagonists. This constant is the concentration of the drug that binds to 50% of the available receptors; the lower this concentration, the greater the affinity the drug has for the receptor. Starting on line 4 are the changes in second messenger levels as a function of agent concentration, as specified by the parameters $V_{max}$, $K_{act}$, and NSA, outlined in the preceding section. All available data for a given composition can be included in this file.

Efficacy Values

Efficacy values are stored in a file (e.g., "K_es") having the following format:

| Line 1: | D1 | D2 | α1 | α2 | β1 ... |
|---|---|---|---|---|---|
| Line 2: | cAMP | cAMP | . | . | . |
| Line 3: | $K_E$ | $K_E$ | | | |
| Line 4: | PI | PI | | | |
| Line 5: | $K_E$ | $K_E$ | | | |
| . | | | | | |
| . | | | | | |
| . | | | | | |

As described below, efficacy values ($K_E$s) are calculated in the med_fx.c program. $K_E$s in file k_es can be determined, e.g., using a $K_E$ from a known interaction of the receptor and a given drug or an analog, can be averaged over many known $K_E$s at the receptor, or can be estimated based on molecular-level interactions.

Neurohumoral Milieu.

This file, termed neur_hum, contains data in the following format:

| Line 1: neurotransmitter$_1$ | concentration$_1$ |
| Line 2: neurotransmitter$_2$ | concentration$_2$ |
| Line 3: neurotransmitter$_3$ | concentration$_3$ |

This is included as an input file both because neurohumoral stimulation can significantly affect cell functioning, and because the effects of antagonists at specific receptors (e.g., D2 blockers) are best understood if tonic, physiological stimulation at these sites is included in the model.

Output of the Medication Effects Program

The medication effects program, e.g., med_fx.c, carries out the following algorithm, for each computational compartment of the model.

(1) If, at the receptor in question, the agent acts as an agonist, then:
  (i) If data on individual second messenger level effects are given (i.e., there are entries on lines 4 and below in the med_char input file described above), the effect on each second messenger is calculated using Equation 2 (above), and
  (ii) $K_E$ is calculated using Equation 5 and Equation 2;
  (iii) If no data on line 4 and below are available, the effect on the messenger is calculated using Equation 6, with values for $K_E$ from the input file k_es;
  (iv) if multiple receptors have effects on a given messenger, individual effects are summed linearly.

(2) If, at the receptor in question, the agent acts as an antagonist, then receptor occupancy due to baseline (neurohumoral) levels of neurotransmitter are adjusted downward using Equation 7 above. Effects of this neurotransmitter are then calculated, using the methodology above.

(3) The effects of neurotransmitters in the neurohumoral milieu that act at receptors unapposed by antagonists are treated as in (1) above.

The output of the medication effects program file (e.g., med_fx.c) is a file containing levels of intracellular messengers that are expressed in GENESIS code. There are also a number of receptors that regulate ion channels directly (i.e., not through intracellular signaling cascades). Direct effects of receptors on ion channels can be included in a process similar to that outlined above.

Network Model of Biologically Realistic Neurons

After implementing a biologically realistic neuron model, one then models the transmission of a signal from that neuron to its neighbors. This aspect of the model can include, for example, the delays in the output of the neuron, either by modeling a neuron's axon by a series of compartments, or since the signal transmission rate along an axon is relatively constant, by delaying the input of the axon's target by an amount proportional to the distance to that target. This aspect of the model can also include changing the synaptic strength between neurons.

A computational model of a neural tissue sample can then be created by representing the steric relationship between neurons withing the sample. This can include representing neuronal cell types present in that sample, and the density of each of those species of neurons within that sample.

Once the steric relationship between neurons has been represented, the next step in constructing a model is to represent patterns of connectivity between neurons. This can include representing how many neurons a particular neuron is connected to and what species those neurons are.

At the most schematic level, a computational model of neural tissue is made up of a large number of independent processing units that send messages to each other. The nature of this model lends itself to implementation in an object-oriented environment. In such an environmentm the different neuronal call types can be represented by different instances of an object class. The properties of each neuronal cell type are then encapsulated as methods within the neural object.

The computational model of neural tissue can be molded in any object-oriented environment. An example of such an environment is GENISIS ("GEneral NEural Simulation System"). An alternative environment for modeling neural tissue is provided by NEURON. Both GENESIS and NEURON are widely available freeware collections of model building tools that can be executed on typical digital computers using a conventional operating system, such as LINUX.

To model neural tissue having a particular pathology, one alters the defining characteristics of a model of normal neural tissue. For example, one can re-define the manner in which selected neruons communicate with neighboring neurons, either by altering connectivity patterns or synaptic response characteristics. Or, one can adjust the ion channel behavior or morphological characteristics of selected neurons. This will redefine the manner in which incoming signals are integrated to produce output signals, i.e., it will change the implicit transfer function. In an object-oriented environment, this can be done, for example, by changing the corresponding methods encapsulated by the objects.

A psychoactive drug typically functions by either changing the implicit transfer function (e.g., by altering ion channel behaviors) of selected neuronal cell types or changing the communication characteristics (e.g., by changing synaptic properties) of those neurons. In particular, the implicit transfer function and communication characteristics built into a model of diseased neural tissue can be altered to simulate exposure of that tissue to a psychoactive drug. On way to determine the manner in which the model is to be altered pharmacologically, is to perform in vitro tests of the effect of the drug on individual neurons. Alternatively, if one already knew the effect of a drug on a neuron, one could use that knowledge and bypass the need to perform such in vitro testing.

Once a model has been constructed, an initial exicitation is applied to selected neurons. The response has been constructed, an initial excitation is applied to selected neurons. The respons of those neurons to the excitation is communicated to neighboring neurons, which in turn communicate their own responses to their own neighbors. This results in a wave of excitations that unfolds over time. The nature of the excitation changes as the neural transfer functions and communications properites change. As a result, when subjected to the same excitation, normal, diseases, and drug-exposed neural tissue provide different outcomes. A comparison of these different outcomes provides a basis for predicting the effect of a particular psychoactive drug on a particular disorder.

For example, one can alter a model of discussed neural tissue to simulate exposure of that tissue to a drug. The altered model and the unaltered model are then subjected to the same initial stimulus (e.g., a stimulus associated with a particular behavioral task). This results in two outcomes, which will be referred to as the diseased outcome and the treated outcome respectively. If these two outcomes are the same, one can infer that the drug will be ineffective in treating the diseased neural tissue.

If the treated outcome and the diseased outcome differ, it may be unclear whether the effect of the drug was beneficial or detrimental. In such a case, it is useful to apply the same initial stimulus to a model of normal tissue to obtain a normal outcome. The normal outcome can then be compared with the treated outcome. If the treated outcome is similar to the normal outcome, one can infer that the drug will be beneficial in treating a disease modeled by the perturbation.

Drug Screening

Figure 12:
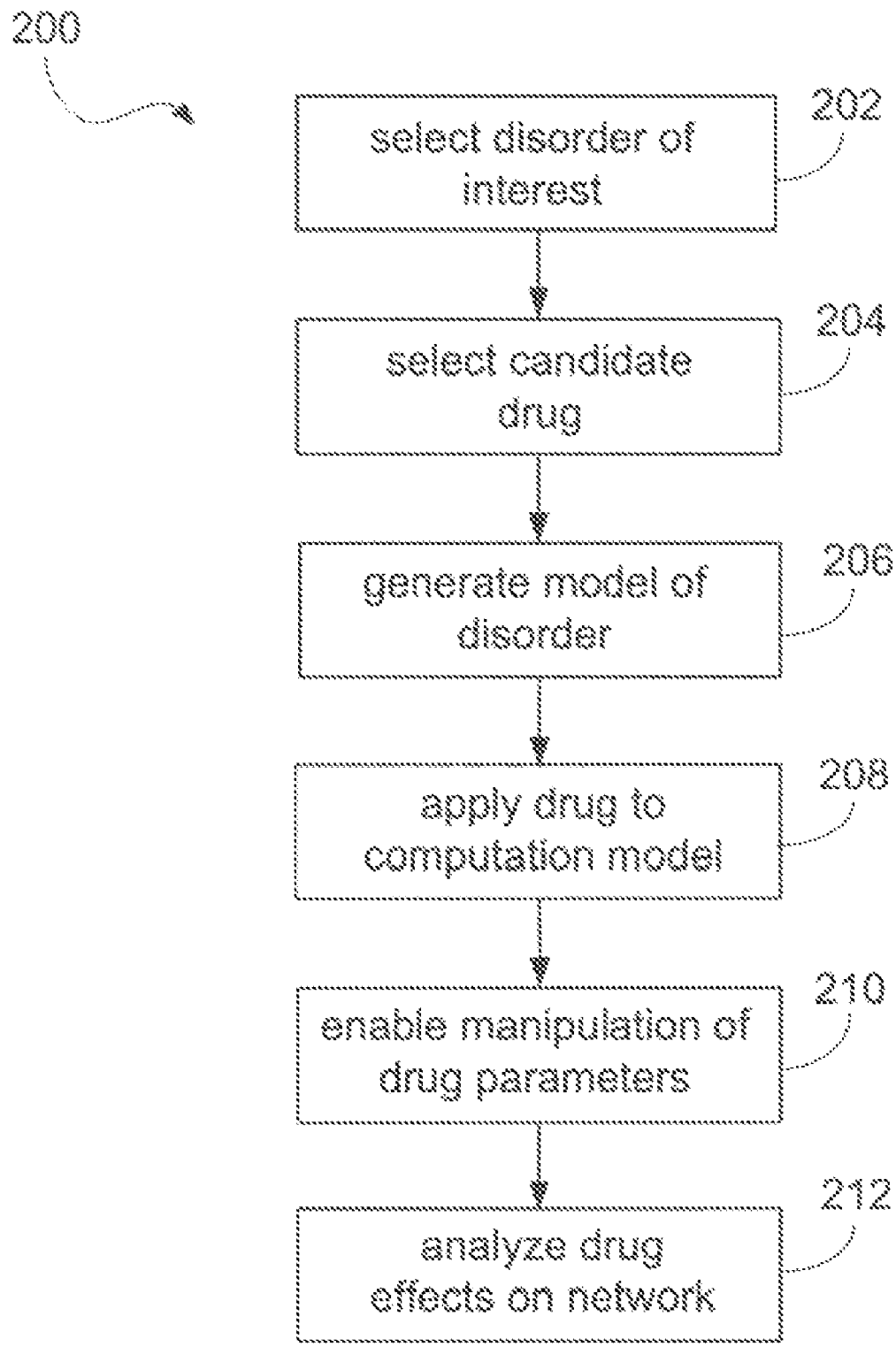
FIG. 12 is a detailed flow diagram of the computational drug screening or discovery process.

A computational drug screening or discovery process 200, illustrated in FIG. 12, is implemented using the general computational methodology described above. The process 200 includes selecting (step 202) a medical disorder to be studied, e.g., schizophrenia. A known drug composition is selected (step 204) as a test or potential drug composition for the medical disorder. A computational network model, in which rapid screening of test drug compositions can be performed, is generated (step 206). The effects of the test composition are then applied (step 208) to the computational network model thus generated. The effects of the test composition on the network are then analyzed and evaluated (step 212). The new systems and methods of drug screening processes are discussed in greater detail below.

Medical Disorders

Computer-based computational and neural network models provide a basis for studying numerous psychiatric and neuropsychiatric disorders, such as schizophrenia, Alzheimer's disorder, bipolar disorder, seizure disorders, diffuse cerebral atrophy, and obsessive-compulsive disorder, at both microscopic and macroscopic levels. Various medical disorders and mental disorders, such as schizophrenia, Alzheimer's disease, bipolar disorder, and the like, can be modeled using the new computational systems and methods. Accordingly, these computational systems and methods can be used to screen potential drugs for the treatment of any disorder for which behavior or physiological changes can be modeled in a network model.

Schizophrenia

Schizophrenia is a heritable disorder of the brain thought to result from abnormalities that arise early in life and that disrupt the normal development of the brain. These abnormalities manifest themselves as structural differences between a schizophrenic brain and a healthy brain. For example, schizophrenic brains tend to have larger lateral ventricles and correspondingly smaller volumes of neural tissue than normal brains. It is believed that the chemical nature of the schizophrenic brain, and in particular the manner in which it processes certain neurotransmitters, such as dopamine, is also different.

The effects of endogenous substances, such as dopamine, on normal functioning of the brain have been gathered by assessing how such chemical compositions alter the physiologic functioning of neurons. Accordingly, altered physiological functioning induced by such compositions can be simulated in biologically realistic neurons of the model.

Symtomatically, schizophrenia can be characterized by many functional deficits. Schizophrenic symptoms are divided into negative and positive categories. Negative schizophrenic symptoms consist of behavioral deficits such as blunting of emotions, language deficits, and lack of motivation. Laboratory data suggests that schizophrenics with negative symptoms may have reduced brain activity in the prefrontal cortex. Positive schizophrenic sympoms include hallucinations, delusions, and bizzare behavior. Tests performed across a variety of modalities suggest that delusion and hallucinations (e.g., hearing voices), are associated dysfunction in the temporal lobes, a part of the brain linked to articulated language.

Biochemical factors are believed to underlie a number of schizophrenic and psychotic symptoms. For example, excessive production of dopamine is believed to play a role in the schizophrenic brain. Neurotransmitters interacting with certain receptors mediate the transfer of chemical information between neurons. It is thought that when anti-schizophrenic drugs block dopamine receptors, the symptoms of schizophrenia are reduced. Five dopamine receptors, D1, D2, D3, D4, and D5, has been discovered. Their function is to bind to dopamine, which triggers changes in the metabolic activity of the postsynaptic nerve cells.

Dopamine antagonists are drugs that block dopamine receptors. Examples of dopamine antagonists include neuroleptics, such as chloropromazine, (THORAZINE® manufactured by GLAXOSMITHKLINE®). Various studies indicate that controlling dopamine and dopamine receptors alleviates symptoms of schizophrenia. THe effectiveness of clozapine, a high affinity D4 receptor antagonist, has called into question the traditional assumption that antipsychotic medications exert their effects via action that the D2 receptor alone. However, a compound created to be a highly selective antagonist at the D4 receptor (L-745870) was seen to be ineffective. Antipsychotic agents like clozapine are probably effective not strictly because of antagonism at any one receptor, but because of their constellation agonisms and antagonisms at dopamine and other neuroreceptors.

Network Models of Medical Disorders (Schizophrenia)

Figure 13:
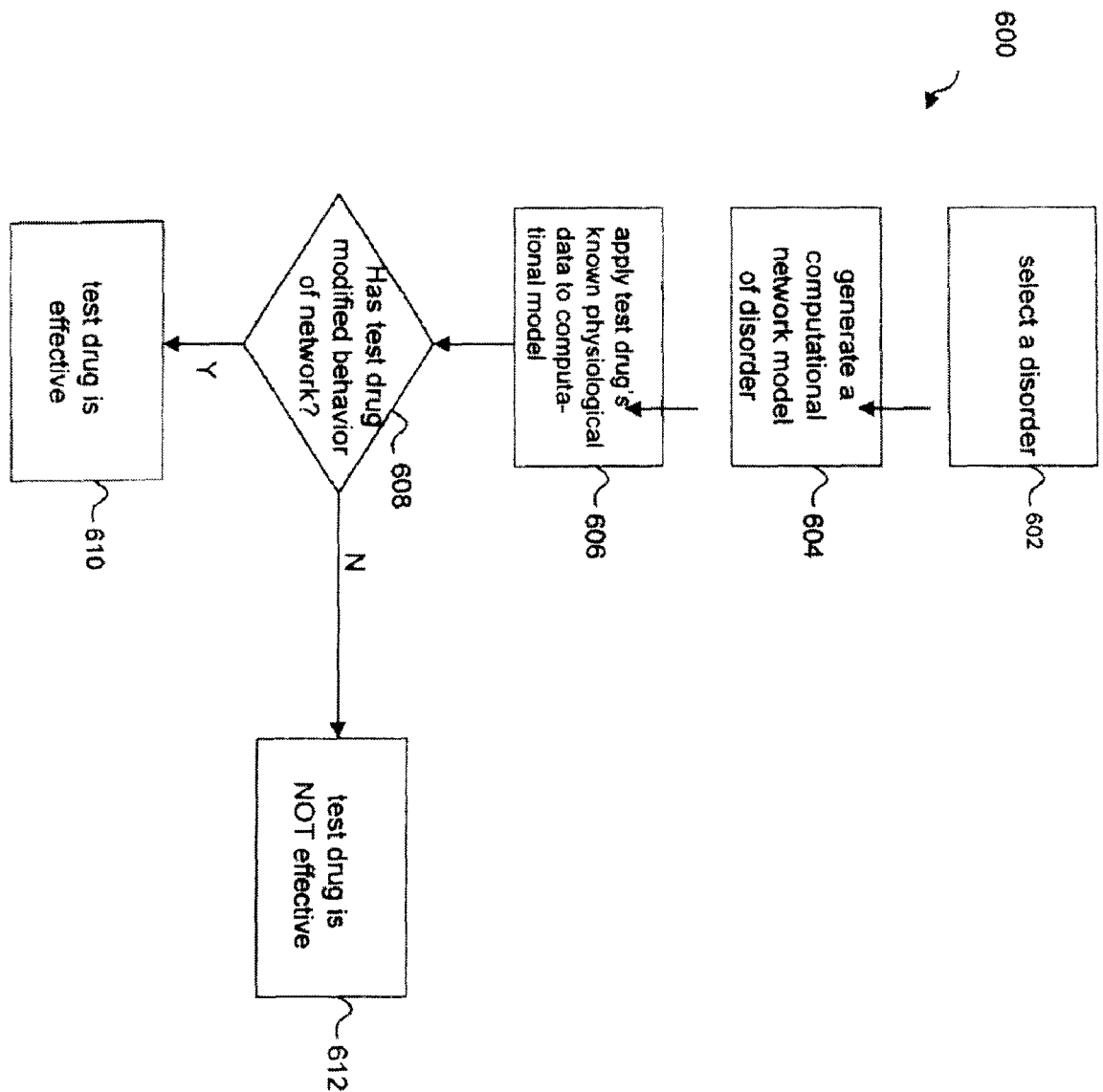
FIG. 13 is a flow diagram for applying potential drug effects to the computational model of FIG. 12.

Referring to FIG. 13, a computational drug screening method 600 includes evaluation of the potential efficacy of a test composition as a psychiatric medication by incorporating that composition's cellular level effects on biologically realistic neuronal behavior in a computational model of neural tissue having a large number of biologically realistic neurons. This is followed by examination of the emergent "macroscopic" behavior of the tissue. As described previously, given that such models are not exact representations of the human brain, the computational drug screening method 600 identifies test compositions that are candidate therapeutic compositions. Accurate assessment of test compositions is further increased by implementation of biologically realistic neurons as described above and the effects of the test composition on their simulated intrinsic properties.

The computational drug screening method 600 includes selecting (step 602) a disorder to be studied (e.g., a psychiatric or neurological condition in question such as schizophrenia). A computational network model that manifests the characteristics of, in this case, schizophrenica is generated (step 604).

Once the computational network model has been generated, information about the known effects of the test composition or physiological neurons is incorporated into the constituent biologically realistic computational neurons of the computational nework model (step 606). Details of this step are described below in connection wiht FIG. 15.

The simulated behavior of the psychiatric or neurological condition is then observed to determine if the behavior of the computational network model has been changed for the better (step 608). If the behavior indicative of the disorder has decreased, the test composition is classified as a candidate drug (step 610). For example, in a computational netowrk for schizophrenia, if the network shows fewer instances of "hallucinatory" pattern recognitions, the test composition is classified as a candidate drug for treatment of schizophrenia (step 610). Similarly, in a computational network model for Alzheimer's disease, improved memory recall, or a less precipitous decline in memory performance, would indicate that the test composition is potentially an effective treatment of Alzheimer's disease. On the other hand, if no beneficial behavior is observed in the network model, the effectiveness of the test composition cannot be conformed (step 612).

To generate a computational network model (step 604) manifesting the characteristics of the psychiatric or medical condition in question, existing models can be used or new ones can be created.

For example, one way to construct a computational model for Alzheimer's disease is to modify a model of a healthy brain by deleting neural synapses in a manner consistent with neuranatomic research findings on the condition of neural tissue in Alzheimer's patients. This results in a computational network model that exhibits a pattern of memory deterioration similar to that seen in patients afflicted with its disease. In other network models, compromised memory recall can be exhibited in a computational network model for this disorder.

Figure 14:
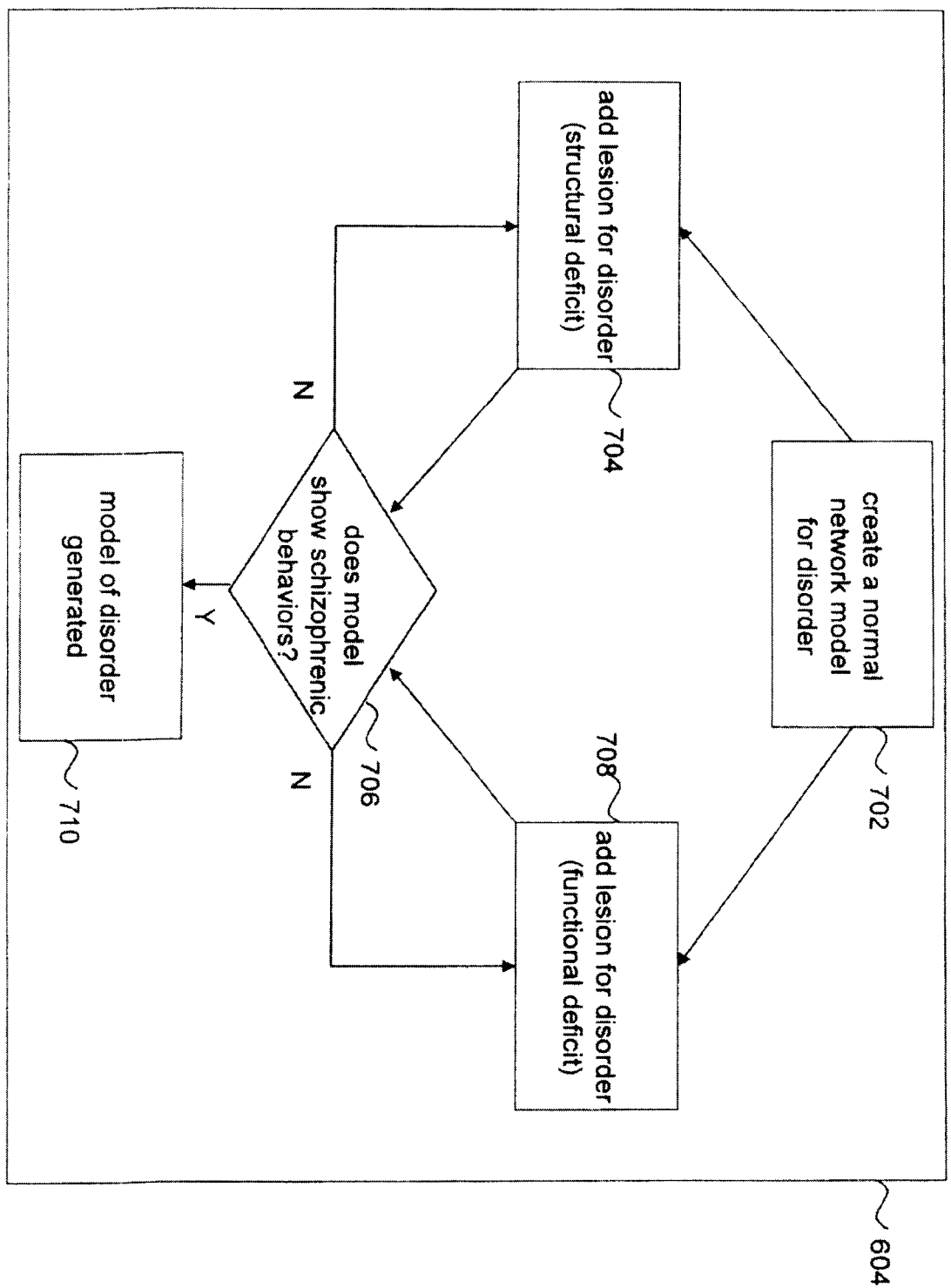
FIG. 14 is a flow diagram for generating a computational network model of a disorder in the computational drug screening process of FIG. 12.

In the case of a schizophrenia model, illustrated in FIG. 14, a network model with "pruned" neuronal connections can be built; this is one of the neural abnormalities thought to underlie schizophrenia. The resultant computational network model exhibits pattern recognition behavior suggestive of hallucinations.

In particular, to construct a neural computational network model that can simulate the cognitive functions of a schizophrenic brain, a network model for a normal brain that can perform basic cognitive functions is first generated (step 702). Then, the network is "lesioned" (step 704) in a manner corresponding to the microanatomic changes seen in actual clinical pathological studies of schizophrenia. For example, the network can be lesioned by removing some of the neurons, or by altering connections between existing neurons. Additionally, abnormalities that are not structural in nature, but nevertheless affect the functioning of neurons can be applied (step 708). Such "functional lesions" can include, for example, degrading the functional characteristics of the computer-modeled biologically realistic neurons in ways analogous to what is observed in neurons of humans afflicted with schizophrenia. Other functional lesions include simulating high dopamine levels by, for example, incorporating the effect of dopamine on the manner in which it affects ion channel behavior, and thus their signal integrating properties.

If by adding structural and/or functional lesions (steps 704, 708), a computational network model showing schizophrenic behaviors is generated (step 706), we would say a model of the disorder has been generated (step 710). Various computational network models can be implemented as described in greater detail below with references to FIGS. 13-14.

By applying pathological lesions to a computational network model, one can generate a computational network model that manifests the characteristics of schizophrenia (step 604). As described previously, schizophrenia effects a large range of mental activities, adversely impacting functions as diverse as attention, memory, language production, and emotion. Schizophrenia has been associated with many different brain regions, particularly the frontal areas and the hippocampus. Schizophrenia is best understood as a distributed dysfunction in which multiple brain areas pathologically interact with each other.

Although no consensus on the etiology of schizophrenia has been reached, a number of factors are suscepted. These include neurodevelopmental dysregulation, excessive dopamine, and various environmental stressors. In step 704 and 708 of FIG. 14, one or more pathological lesions are introduced into the computational network model of schizophrenia in a manner consistent with these suspected etiologies.

In neurodevelopmental dysfunction of schizophrenia, excessive cortico-cortical pruning may be a factor. Thus, leasioning (step 704) can be simulated by overpruning of a normal computational network model. An example of this approach to creating a lesioned model is to use an attractor network to create a computational network model of semantic priming, a subject is exposed to a priming word. The subject is then asked to identify a target word that is semantically related to the priming word. An attractor network is created in which a semantic class is operationalized as particular subset of neurons of the model. The details of the model are given in Siekmeier and Hoffman, "Enhanced Semantic Priming in Schizophrenia: a Computer Model Based on Excessive Pruning of Local Connections in Association Cortex," British Journal of Psychiatry, vol. 160:345-350 (2002), the contents of which are herein incorporated by this reference in their entirety.

At baseline, the semantic priming model showed semantic priming behavior similar to that seen in control clinical populations. When this model is leasioned by selectively removing neural connections in way similar to that seen in a schizophrenic brain, the percentage of correctly identified target words increases in a manner consistent with that measured schizophrenic populations. If the priming behavior of such a model, when exposed to a test composition, were to return to baseline, one could infer that the test compsition would be potentially effective in alleviating symptoms of schizophrenia.

Another way to apply a lesion (step 708) is to introduce a functional deficit, e.g., one resulting from excessive dopamine levels in a network model of a normal brain. An example of this follows.

The pre-frontal cortex and its dense dopamine activity are involved in working memory functions. Task-related electrical activity in the pre-frontal cortex is modulated by dopamine, mainly via the D1 receptor, with dopaminergic midbrain neurons activated at the onset of working memory tasks and dopamine levels in the pre-frontal cortex increasing during performance of such tasks. Blockage of dopaminergic input to the pre-frontal cortex or of dopaminergic D1 receptors in the pre-frontal cortex distributes delay-task performance. Dopamine, at physiological levels, appears to stabilize actual neural representations in pre-frontal cortex circuits during tasks involved in working memory, thereby rendering them robust against interfering stimuli and noise.

To mimic the dopamine-modulated ionic currents that could give rise to increased stability of neural representations, a network model of the pre-frontal cortex is constructed. The computational network model of the pre-frontal cortex includes multicompartment neurons equipped with Hodgkin-Huxley-like channel kinetics that can reproduce in vitro whole cell and in vivo recordings from a pre-frontal cortex neurons. dopaminergic effects on intrinsic ionic and synaptic conductance are implemented in the model based on the in vitro data in a variety of ways. Specifically, dopamine shifts the activation threshold of a persistent Na+ current toward hyperpolarized potentials and delays the inactivation of this current. This shift appears to contribute to dopamine-induced increases in firing rate and reduced adaptation observed in vitro., Dopamine-induced shifts of the activation threshold can be modeled by reducing K+ conductance; this change relies on the fact that dopamine decreases slowly inactivating K+ current in prefrontal cortex pyramidal cells. Dompamine, acting at the D1 receptors, increases N-methyl- D-aspartate (NMDA)-like synaptic curents in the prefrontal cortex. This effect can be molded as an increased synaptic NMDA conductance in the computational neurons. In addition, dopamine effects can be modeled by increasing glycine and g-amino butyric acid (GABA) synaptic conductance based on dopamine induced enhancement of GABAA (GABA, type A)-like synaptic currents in the pre-frontal cortex. Further, based on data that dopamine may heighten spontaneous firing activity of GABA neurons in pre-frontal cortex, the background firing rate ("noise" level) of GABAergic inputs can be increased in the computational network model.

Consequently, dopamine strongly enhances high, delay-type activity. The dopamine-induced changes in the biophysical properties of intrinsic ionic and synaptic conductance increase stability of activated representations in pre-frontal cortex networks. Simultaneously, the dopamine-induced changes retain control over network behavior and respond to task-related stimuli. The schizophrenic condition is simulted by exposing the model of supra-normal levels of dopamine. This causes representations to become "overly" stable, resulting in response perserveration and behavioral sterotypies characteristic of schizophrenic patients.

Other disorders can also be computationally modeled.

For many neurological and psychiatric conditions the dysfunctional brain area may be known, but the manner in which neurobiological abnormalities give rise to this dysfunction is not known. For example, it may be unclear whether the symptomatology of a particular illness arises from deficiencies in the GABAergic system, deficiencies in the glutamatergic system, abnormalities in serotonergic tone, or some combination of these. Thus, in the model, lesions of various magnitudes are applied to elements of each of these systems individually and in combination—that is model parameters controlling the characteristics of the GABA system, characteristics of the glutamatergic system, and dopaminergic tone are systematically varied and thus the "parameter space" is exhaustively searched.

For example, the density of GABAergic synaptic projections, can be altered. This can be implemented by varying its density parameter in the model through a range of values. Similarly, elements of the glutamatergic system, such as AMPA receptor density or NMDA receptor density, can also be varied. Simultaneously, neurotransmitter levels can be varied between subnormal and supranormal levels. As described previously, the concentrations of modulatory neurotransmitters in the neurohumoral milieu are explicit inputs to the model. The manner in which the effects of these neurotransmitters are made known to the model is identical to the way that medications are included. Thus, changing the ambient serotonin level can be modeled simply by changing the value of its concentration term.

In modeling neurological and psychiatric conditions, parameter values along many dimensions can be varied—in the example given, one dimension is related to the GABAergic system, two are related to the glutamatergic system, and one to the serotonergic system. With, for instance, 20 gradation per parameter, this creates a large number of iterations, or parameter sets ($20^4$=160,000). Using measures of model behavior that index pathological functioning, one can decide which of the parameter sets produces behavior most like the illness in question; any model behavior—e.g. based on oscillatory activity or psychological task—that distinguishes normal from diseased behavior can be used. This, then is the model to be used in the subsequent steps of the drug screening process.

Figure 15:
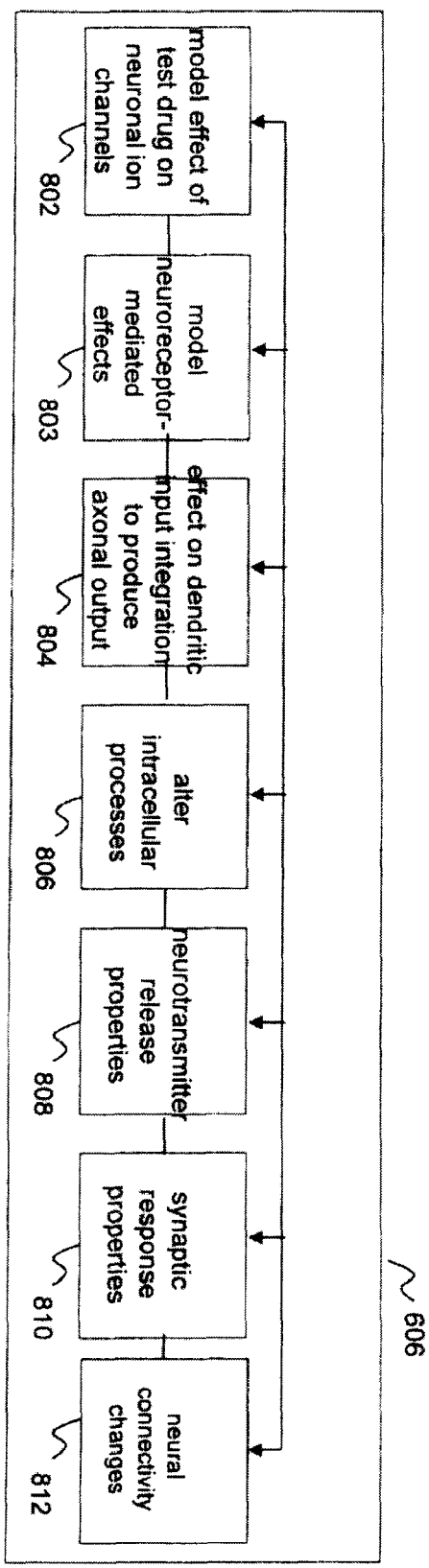
FIG. 15 is a diagram model of the parameters that can be chaned for simulating the effect of a drug.

In most cases, generating a computational network model of schizophrenia includes creating a normal computational network model (step 702) and adding structural or functional lesions to the network model (steps 704, 708) to generate a computational network model of schizophrenia (step 710). Referring back to FIG. 13, once the computational network model of schizophrenia has been generated (step 604), a test composition, e.g., a known compound, is selected and incorporated into the network (step 606) by applying information about its known effects on individual physiological neurons to the model's constituent computational neurons. This can be carried out in a number of ways, as illustrated in FIG. 15. For example, one approach is to model (step 802) the effects of the test compositions directly on ion channels or synaptic conductances, as illustrated in Example 3 for the drug Chlorpromazine.

A second way (step 803) is to simulated contacting neurons with drugs drugs by way of representing their effects on cell membrane receptors, which are then transduced, via intracellular messaging, to changes in ion channel behavior, this is described in detail on pages 18-28.

A third approach for applying the effects of a test composition is to model (step 804) the effect that the test composition is known to have on the integration of dendritic inputs to produce an axonal output, i.e., a "transfer function." This third method is particularly useful when modeling Hopfield neurons. For example, the effects of a central nervous system stimulatn such as methylphenidate (RITALIN®) can be modeled by altering the transfer functions of the network's constituent neurons. Methylphenidate has a notably calming effects on hyperactive children and a "focusing" effect on those with attention deficit disorders. Using this approach (step 804), methylphenidate's ability to enhance responsivity of cells can be modeled as an increase in the gain of those cell's transfer functions.

A fourth approach is to alter (step 806) model parameters associated with simulation of intracellular processes, such as receptor activations and gene transcription. These processes may control receptor expression, and this method may be useful for modeling the effects of antidepressants. A fifth approach simulates application of a test composition by modeling changes (step 808) in the neurotransmitter release properties of neurons in the network model. A sixth approach simulates application of a test composition by changing (step 810) the synaptic response properties of neurons in the network model. A seventh approach simulates the manner in which a medication may change neural connectivity (step 812), either by enhancing neurotrophic drive, stimulating the "sprouting" of dendritic or axonal processes, or by changing the processes by which these connections are eliminated.

In applying a test composition's physiological data to the relevant disorder's computational model (steps 802 through 812), the information of the test composition's effects on individual neurons or its neuron-to-neuron (synaptic) behavior may be unknown, In such cases, it may be necessary to first gather data experimentally by in vitro exposure of neurons to the test composition, and to measure the effects of the test composition on individual neuron behavior and synaptic response characteristics.

Referring back to FIG. 13, once the computational network model has been joined with data on the test composition's known effects (step 606), it becomes possible to determine whether application of the drug has modified the behavior or functioning of the network model for the better (step 608). For example, an Alzheimer's Disease model could show a decrease in behaviors analogous to poor memory performance. In a seizure disorder model, the network model may exhibit altered oscillatory behavior. To this end, groups of model performance behaviors, analogous to groups of well-defined clinical performance or behavior measures, may be employed. In particular, the gross electrical behavior of a computational model, as measured by a simulated local field potential or simulated electroencephalogram (EEG) can be used as an outcome measure that is analogous to EEGs or MEGs recorded clinically, or to implanted electrodes. The extent to which a test composition, implemented in a computational model, decreases seizure-like model behaviors in the model, that test composition is potentially effective at treating epilepsy or other seizure disorders.

Also, in a schizophrenic model, the network model may exhibit altered oscillatory behavior. For example, it has been shown using both EEG and MEG techniques, that schizophrenics have an inability to support gamma frequency (approximately 40 Hz) oscillations. Clinical experiments in which schizophrenic patients and controls were exposed to 20, 30, and 40 Hz auditory click trains quantified this deficit, and showed that it was unique to the 40 Hz frequency. Thus, the extent to which a test composition, implemented in a computational model, decreases this oscillatory abnormality, the test composition is potentially effective at treating schizophrenia.

Figure 16:
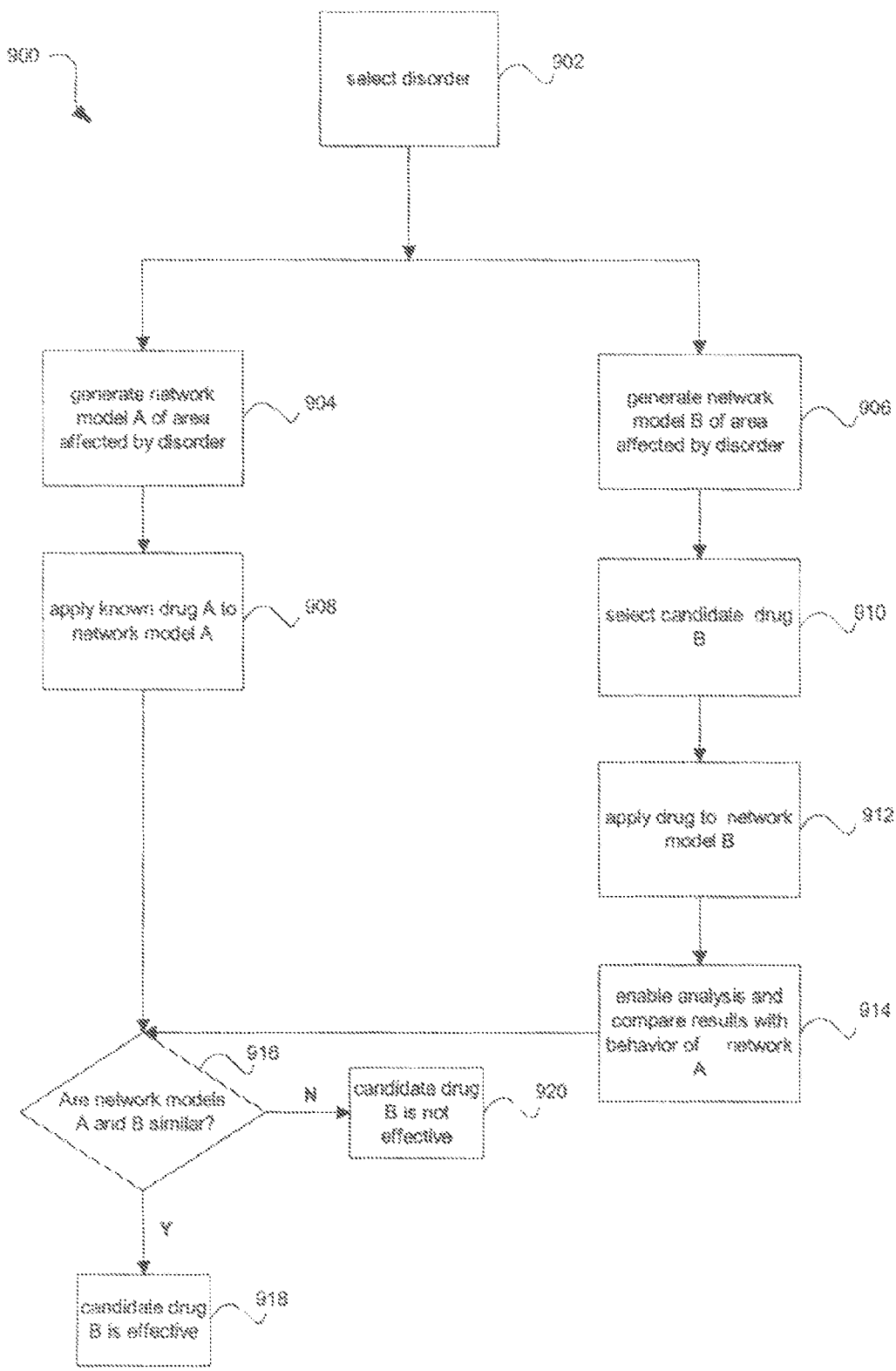
FIG. 16 is a flow diagram of another computational drug screening or discovery process.

Referring to FIG. 16, a second method for using computational network models to evaluate or screen potentially effective test compositions includes comparing the effects of test compositions with the effects of medications already known to be effective.

In this method (step 900), after a disorder is selected and identified (step 902), a computational model of an area of the brain known to be dysfunctional in the disorder in question, i.e., schizophrenia, is generated (steps 904 and 906). Two models A and B can simultaneously generated. As described previously for schizophrenia, the prefrontal cortex or temporal lobes could be modeled, whereas for Alzheimer's disease, the basal forebrain structures could be modeled. In this embodiment, the computational network models are not developed based on analogies with clinically observed behaviors (as in the systems and methods described with respect to FIGS. 14-16). Instead, the neuropathology of the brain structures involved in brains suffering from the disorder is modeled based on what is already known at the neuroanatomic and neurophysiologic level.

Once the computatonal network model of an area of brain disorder is generated (step 904), a known drug A is applied (step 908) to the computational network model A. As described previously, the virtual application of a drug compound to the constituent computational neurons of the model can draw on: the manner in which receptor-mediated events neurophysiologic properties of ion channels synaptic level; data on changes in the neurophysiologic properties of ion channels triggered by receptor activation; or on the effects of certain classes of chemical on neuronal firing rates. Thus, the computational network model information about compositions that are known to be effective in treating schizophrenia is applied (step 908) as discussed in connection with step 606 of FIG. 13. For example, when the model is one of schizophrenia, the effects of various neuroleptics (e.g., THORAZINE®, HALDOL®, ZYPREXA®) can be simulated in step 908.

Similarly, a test composition B is selected (step 910) for computer-based screening. The physiologic information about the test composition is applied (step 912) to the network model B. The resultant network behavior is then examined and analyzed (step 914). After the effects of the known effective medication or drug are applied (step 908), the functioning of both network models A and B are examined by comparing the network behaviors (step 916) of computational network models A and B. Specifically, network behavior common to both the known drug and the test composition are noted. This can include, for example, any characteristic spatial patters of neuron activation, or any distinctive temporal patterns in the manner in which the neural patters of activation transition from one state to another.

To the extent that the behavior of the computational network models resemble each other, the test composition B can be classified as being potentially effective in treatment of the disorder (step 918). Conversely, to the extent that computational network models differ in behavior, the test composition B can be classified as being ineffective in the treatment of the disorder (step 920).

In this second drug screening method (step 900), the screening of the test compositions is based on a direct comparison with medications known to be effective. This second method 900 achieves this by first creating a computational network model of dysfunctional neural tissue and subsequently applying, to the computational network model thus created, information about drugs known to be effective in treating this disorder. The behavior of the system under the influence of the unknown test composition, when composed to the resultant model of the known drug, provides an indication of the test compositions potential effectiveness for treatment.

Computer Implementations

In this embodiment described above, the computational steps of the new systems and methods are implemented on a computer system or on one or more networked computer systems to provide a powerful and convenient facility for forming and testing computational network models of biological systems.

Figure 17:
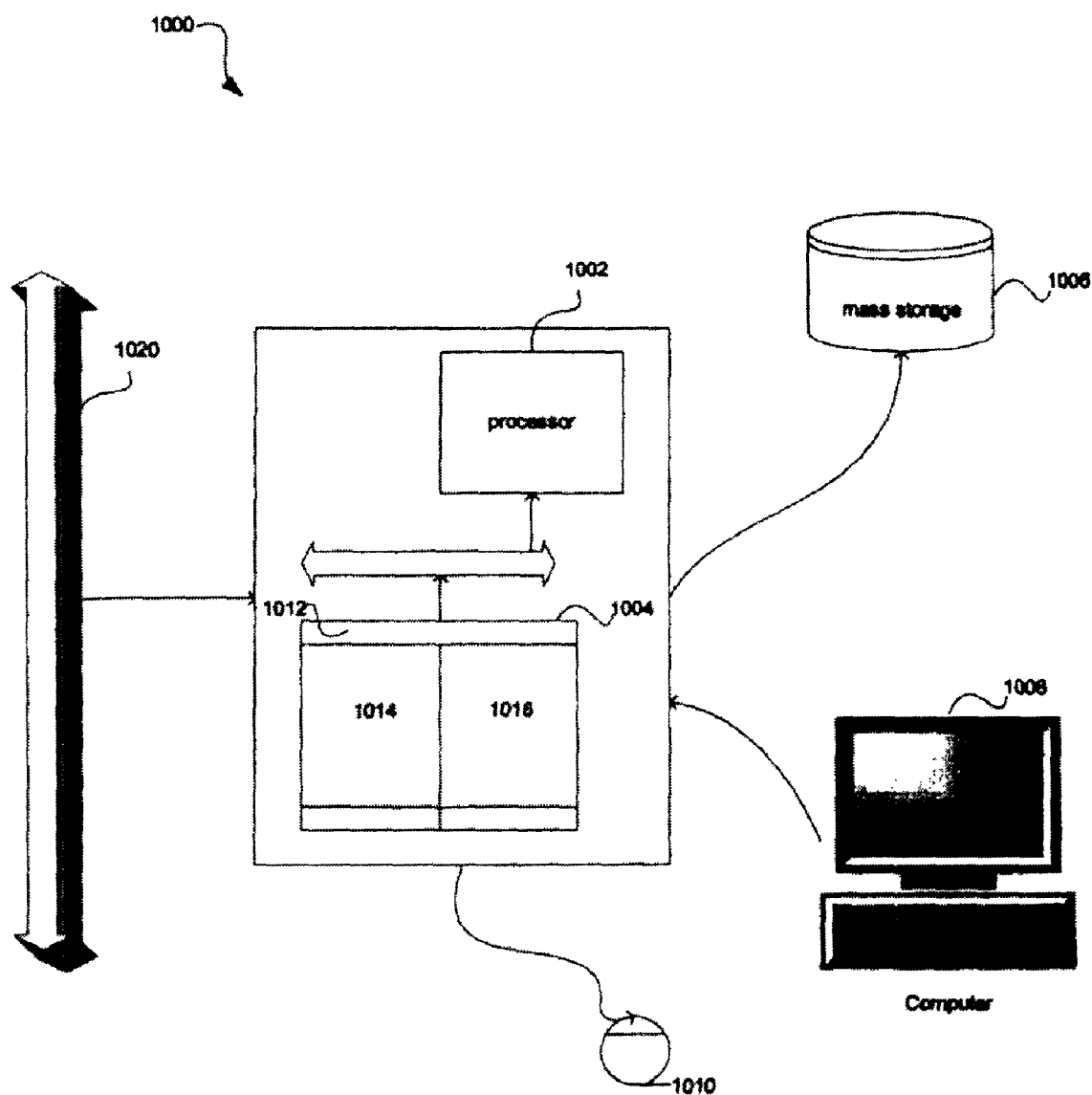
FIG. 17 is a computer system used to carry out the computational test screening process of FIG. 12.

FIG. 17 illustrates an exemplary computer system 1000 suitable for implementation of the new system and methods.

The computer system 1000 is illustrated as a single hardware platform including internal components and being linked to external components. The internal components of the computer system 1000 include a processor element 1002 interconnected with a main memory 1004. For example, computer system 1000 can include an Intel® Pentium based processor.

The external components include a mass storage 1006. The mass storage 1006 can be one or more hard disks packaged together with the processor 1002 and the memory 1004. Other external components include a user interface device 1008, which can be a monitor and keyboard, together with a pointing device 1010, which can be a "mouse," or other graphic input devices (not illustrated). Typically, the computer system 1000 is also linked to other local computer systems via a bus 1020, remote computer systems, or wide area communication networks, such as the Internet. The network link allows the computer system 1000 to share data and processing task with other computer systems.

Several software components, which will be described in greater detail below, are loaded into memory during operation of this system. The software components collectively cause the computer system 1000 to function according to the new methods of this invention. These software components are typically stored on the mass storage 1006. Alternatively, the software components may be stored on removable media such as floppy disks or CD-ROM media (not illustrated). A software component 1012 represents an operating system (OS) responsible for managing computer system 1000 and its network interconnections. The OS can be, e.g., of the Microsoft® Windows, i.e., Windows® 95, Windows® 98, Windows® NT, or a Unix operating system, such as Sun Solaris®. A software component 1014 represents common languages and functions present on the computer system 1000 to assist programs implementing the methods specific to this invention. Various programming languages that can be used to program the analytic methods of this invention include C, C++, and the like.

The new systems and methods are programmed in mathematical software packages, which allow symbolic entry of equations and high-level specification of processing, including special algorithms to procedurally program individual equations or algorithms. The computational models described previously can be implemented, using freeware packages such as GENESIS (General Neural Simulation System). GENESIS is a general purpose simulation platform developed to support the simulation of neural systems ranging from complex models of single neurons to simulations of large networks made up of more abstract neuronal components. Most GENESIS applications involve realistic simulations of biological neural systems. Other simulation software such as NEURON, described in Hines, et al., "The NEURON simulation environment, Neural Comput., 9, 1179-1209 (1997), may be used. A software component 1016 represents the analytical methods as programmed in a procedural language or symbolic package such as GENESIS.

Figure 18:
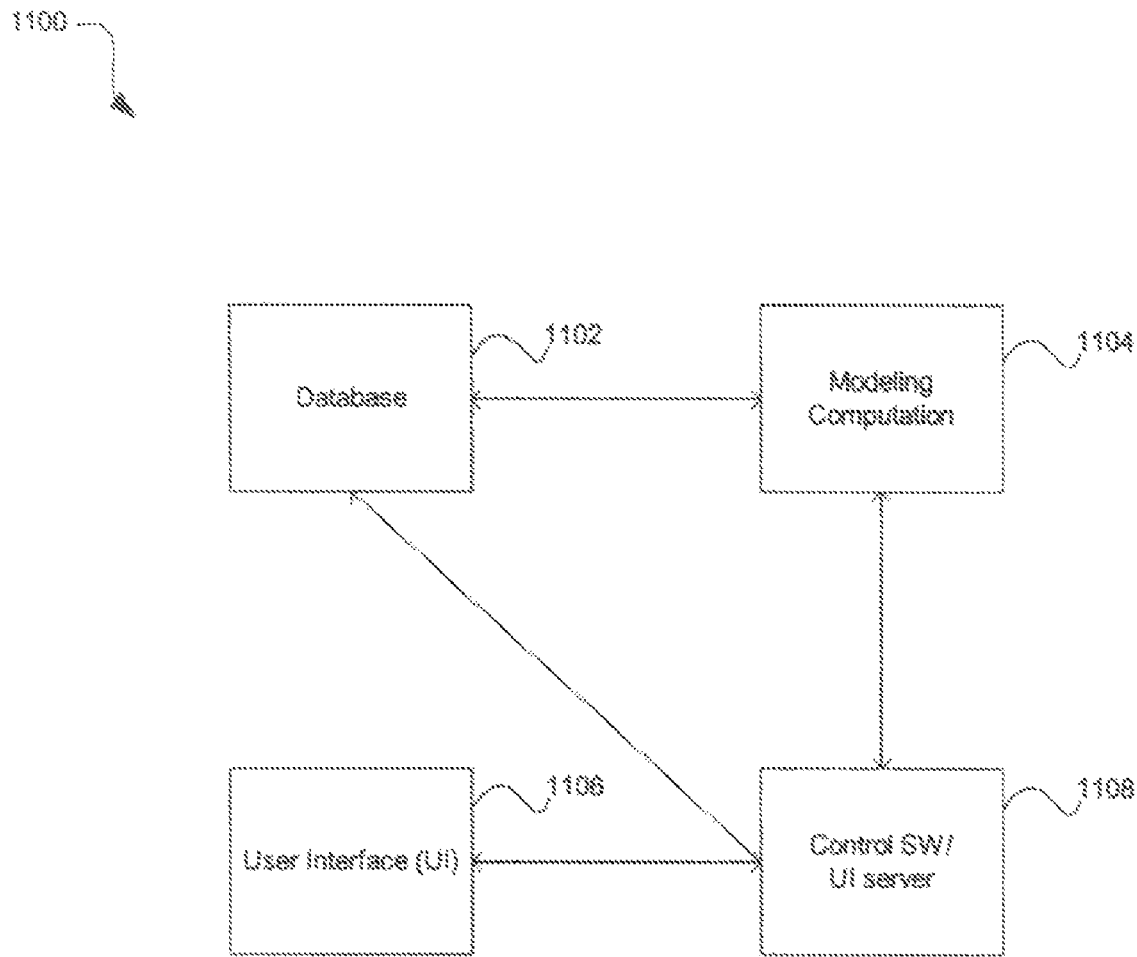
FIG. 18 is a software module used in the computer system of FIG. 17.

Referring to FIG. 18, the software implementation of the computer system 1000 may include a number of separate software components interacting with each other. An analytic software component 1102 represents a database containing data for the operation of the computer system 1000. Such data generally includes, but is not necessarily limited to, results of prior computations, network model data, and/or clinical data. An analytic software component 1104 represents a data reduction and computational component that include one or more programs which execute the analytic methods, including the methods for testing a network model, as described in FIG. 13 and 16. Analytic software component 1106 includes a user interface (UI), which provides a user of the computer system 1000 with control and input of test network models, and, optionally, known data related to the drug screening processes. The user interface may include a drag-and-drop interface for specifying hypotheses to the system as shown in FIG. 1. The user interface may also include loading of network models or clinical data from the mass storage components (e.g., the hard drive), from removable media (e.g., floppy disks or CD-ROM), or from a different computer system communicating with the computer system 1000 over a network (e.g., LAN, WAN, wireless). An analytic software component 1108 represents the control software, also referred to as UI server for controlling other software components of the computer system 1000.

Application of Computer Model to Drug Synthesis

As described above, a biologically realistic model of neural tissue can be applied to modeling the effect of a drug with known characteristics on diseased neural tissue to see if a desirable outcome occurs. However, it is also possible to run this process "in reverse," i.e., to begin with a desirable outcome and ask what cellular level parameters must be changed to yield that desired outcome. The answer to this question provides guidance as to the characteristics that are desirable for drugs that will prove useful in the treatment of the modeled disease. These desirable characteristics, in turn, inform the synthesis of novel candidate drugs to be used for treating the disease. The method, as described below, includes a process to infer a candidate drug that has a set of receptor agonisms and antagonisms efficacious for treating the modeled illness.

For a given model of a neural disorder (e.g., schizophrenia), as described herein, a series of simulated drugs is generated that have a range of affinities for each neuroreceptor or ion channel between its minimum and maximum value. In other words, the parameter space of all possible receptor affinity values is searched vis-a-vis the various simulated drugs. For each simulated drug, disease outcome measures are determined. For example, in the model of schizophrenia, epoch frequency, semantic priming performance, are determined. The trial or trials creating the best performance on these measures is noted. A pharmacologic agent featuring this profile of receptor activities would be predicted to be most useful in treating the disease.

Stated another way, in the biologically realistic model of the diseased tissue, there may be m parameters that can be adjusted, with each of the m parameters being able to take one of n biologically realistic values. These parameters might be, for example, ion channel conductances, or synaptic conductances. The process then identifies those values of the m parameters that result in, for example, a desired epoch frequency. Although the number of combinations of parameter values can become large, it is nevertheless a finite number that can be efficiently searched using a variety of known algorithms for searching discrete valued solution spaces of finite extent.

An analogous process can be used for single cell models. First, a healthy (non-diseased) model neuron is evaluated on a battery of neurophysiologic tests. This is carried out by, for example, applying various inputs (e.g., a simulated fiber volley; spike train stimuli of various frequencies) and quantitatively determining the neuron's response properties (e.g. pattern of axonal outputs). Then, the single-cell model is lesioned in a manner (e.g., at the ion channel or synaptic level) consistent with the known or suspected pathology of the neuropsychiatric illness in question. Then, the parameter space of all possible receptor affinity values is searched, as above. The trial or trials creating the behavior most like the normal neuron on these measures is noted. A pharmacololgic agent featuring this profile of receptor activities would be predicted to be most useful in treating the disease.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Example 1

Construction of a Biologically Realistic CA1 Pyramidal Cell

Using the algorithm described herein under the section entitled "Biologically Realistic Computer Model of a Neuron,", we have constructed a single neuron model with spatially compartmentalized conductances and anatomically realistic dendritic arborizations. We carried this out by writing a program in the C computer language that creates a GENESIS model based on input files containing raw neuroanatomic and neurophysiologic data, as detailed below.

Input files

Dendritic arborizations. FIG. 26 shows the first 25 lines (and header) of a file in the ".swc" format, which specifies dendritic morphology of an actual neuron. This was constructed by visualizing a rat CA1 pyramidal neuron and recording the x, y, and z coordinates of points along the dendritic tree. A single line in FIG. 26 contains seven pieces of information, in this order: 1.) line (segment) number; 2.) type of segment (1=soma, 2=axon, 3=dendrite, 4=apical dendrite, 5=fork point, 6=end point); 3, to 5.) x, y, and z coordinates, respectively, of the beginning point of segment; 6.) radius of segment; 7.)identity of proximal segment (−1 indicates that it is the first, or most proximal, segment).

Ion channel densities. FIG. 27 is a printout of the file "chan_dens," which lists in tabular form the densities of various species of ion channels as a function of distance from the soma. These data were gleaned from the literature, as noted in the file (a pound sign in the leftmost position of a line indicates that it is a comment, and will not be read by the program). Not all density values for all points along the dendritic tree are known with certainty. When it is felt safe to interpolate between known values, an "i" is entered. If no data whatsoever are available, a "−2" is entered; in this case, a default value is used. If not data whatsoever are available, a "−1" is entered; in this case, a default value is used. Data for a number of different neuron types are given. The program described here uses the top eight (uncommented) lines.

Functioning neuron model. The program "makeproto.c" takes the two aforementioned files as inputs, and creates GENESIS-readable code. A schematic of this neuron is shown in FIG. 8. Stretches of dendrite in the actual (biological) neuron without branch points are represented in the computational neuron as straight segments. Ignoring "kinks" in this manner greatly reduces the number of compartments (and computer processing demands) of the resultant neuron. Also, such kinks probably do not contibute to the neuron's computational abilities in a significant way. Thus, the number of compartments in the computational model is significantly lower than the number of segments of the biological neuron. Ion channels are distributed across the dendritic segments based on the data of chan_dens. Each line in the GENESIS readable code output contains information fully specifying one computational compartment, including dimensions, ion channels present, and their densities. The resultant neuron produces a voltage trace, spiking behavior, etc. that can be compared to that of actual neurons.

Example 2

Computer Model of Normal Hippocampus

The hippocampus is divided into four subfields, CA1-4 ("CA" stands for "cornu ammonis," another name for the hippocampus suggestive of its resemblance to the ram's horn on the head of the Egyptian deity Ammon).

A computational model that represents tissue from the CA1 subfield of the hippocampus was constructed as follows.

A computer nodel representing a tissue sample from a rat brain was created. The virtual sample (hereafter, "the sample") extended 154 micros in the septo-temporal and transverse directions, and 634 microns in the direction orthogonal to those two directions. The resulting sample, which extended from the stratum lacunosum-moleculare ("SL") layer of the hippocampus to the alveus, included 400 pyramidal cells and 52 interneurons. The interneurons included 16 paravalbumin ("PV") cells, 6 calbindin ("CB") cells, 9 calretinin ("CR") cells, and 4 cholecystokinin ("CCY") cells. This sample was then simulated by a computational model that did not distinguish between subspecies of each of these species of interneuron, except on the basis of their axonal projection patterns. The dendritic morphology and ion channels distribution for all interneurons were assumed to be the same.

Because of constraints on computational resources, the number of cells in the computer model was 452, only a fraction of the cells in the hippocampus. Even with this limited number of cells, twenty-four hours were required to simulate two seconds of brain activity with a high-speed dual-processor personal computer. However, because the computer model featured many similar cell performing computationally intensive tasks and passing results to other cells, it would have been possible to harness multiple computers operating in parallel. A version of GENESIS, known as P-parallel architectures to cooperate with each other.

Each pyramidal cell modelled using the 64 compartment pyramidal cell modeled described by Traub, et al., "A Branching Dendritic Model of a Rodent CA3 pyramidal neurone." Journal of Physiology 1004, 481: 79-95 Ppt, 1 ). The interneuron cells models were based on the model described by Traub and Miles, "Pyramidal Cell-to-Inhibitory Cell Spoke Transduction Explicable by Active Dendritic Conductances in Inhibitory Cell, "Journal of Computational Neuroscience, 1995, 2(4):291-298. Both models included a representation of the internal calcium ion concentrations, realistic arborizations, and representation of the $Na^+$, $Ca^{++}$, $K^+_{DR}$, $K^+_{AHP}$, $K^+_C$, and $K^+_A$ ion channels. Initial segments of the axons were modeled as compartments, however axons themselves were modeled only as delays.

Population densities of interneuron subtypes in the model for each hippocampal layer were calculated from known population densities. Suitable data obtained from 60 micron hippocampal slices was given by Freund and Buzsaki, "Interneurons of the Hippocampus," Hippocampus, 1996, 6(4): 347-470. Densities of pyramidal cells in the stratum pyramidale of the CA1 subfield are available from Boss, et al., "On the Numbers of Neurons in Fields CA1 and CA3 of the Hippocampus of Sprague Dawley and Wistar Rats," Brain Research, 1987, 406(1-2):280-287. Within a particular stratum, the neuron distribution was modeled as randomly distributed throughout that stratum.

The spatial distribution of synapses between axons and dendrites of the hippocampus was modeled by determining a distribution of axonal arborization associated with particular morphological classes of neurons. Then, for each class of neurons, a distribution of synaptic targets was defined. The synaptic targets were characterized by the stratum containing the target, the targeted neuron species (i.e. pyramidal cell or interneuron), and the synaptic target area (i.e., initial segment, soma, or dendrite). For each species, the spatial bouton densities of the axonal projection cloud were calculated. The distribution of synaptic targets was then used to apportion, to each neuron of a particular species, a distribution of synapses consistent with the spatial bouton densities for that neuron species.

Table 1, reproduced below, summarizes the computer model's assumptions concerning the axonal arborizations associated with neuron species located in particular strata. For example, according to Table 1, the model assumed that 45% of PV neurons in the stratum oriens ("SO") layer of the hippocampus had basket axonal arborizations, 45% had chandelier patterns, and the remaining 10% had bistratified axonal arborizations. CB cells were assumed to be bistratified in the SO, SR, and SL layers and radiatum-projecting in the SR layer. All CB cells in the SL layer and the SO layer were bistratified. CB cells in the SR layer were evenly split between bistratified and radiatum-projecting arborizations. CR cells were assumed to be interneuron projecting in the SO, SP, SL, and SR layers. SOM cells were assumed to have oriens-lacunosum moleculare arborizations in the SO layer and not to exist in any other layer. CCK cells were assumed to be in the SO, SP, and SR layers and were assumed to have basket arborizations in each of those layers. PC cells were assumed to lie only in the SP layer and to have the pyramid cell arborization in that layer.

TABLE 1

| CELL TYPE | HIPPOCAMPAL LAYER | AXONAL ARBORIZATION | PERCENTAGE OF POPULATION |
|---|---|---|---|
| PV | SO | Bask | 0.45 |
| PV | SO | Chan | 0.45 |
| PV | SO | Bist | 0.10 |
| PV | SP | Bask | 0.45 |
| PV | SP | Chan | 0.45 |
| PV | SP | Bist | 0.10 |
| CB | SO | Bist | 1.0 |
| CB | SR | Bist | 0.5 |
| CB | SR | Radi | 0.5 |
| CB | SL | Bist | 1.0 |
| CR | SO | Intr | 1.0 |
| CR | SP | Intr | 1.0 |
| CR | SL | Intr | 1.0 |
| CR | SR | Intr | 1.0 |
| SOM | SO | o-lm | 1.0 |
| CCK | SO | Bask | 1.0 |
| CCK | SP | Bask | 1.0 |
| CCK | SR | Bask | 1.0 |
| PC | SP | Pyra | 1.0 |

Abbreviations for axonal arborizations are as follows: "bask" means "basket," "chan" means "chandelier (axo-axonic)," "bist" means "bistratified," "intr" means "interneuron projecting," "radi" means "radiatum-projecting," and "o-lm" means "oriens-lacunosum moleculare," and "pyra" means "pyramidal axon arborization." Abbreviations for the four layers for the hippocampus are as follows: "SR" means "stratum radiatum," "SP" means "stratum pyramidale," "SL" means "stratum lacunosum moleculare," and "SO" means "stratum oriens." Abbreviations for the neuron classes in Table 1 are as follows: "PV" means "parvalbumin," "CB" means "CCK immunoreactive cell," and "PC" means "pyramidal cell."

Figure 19:
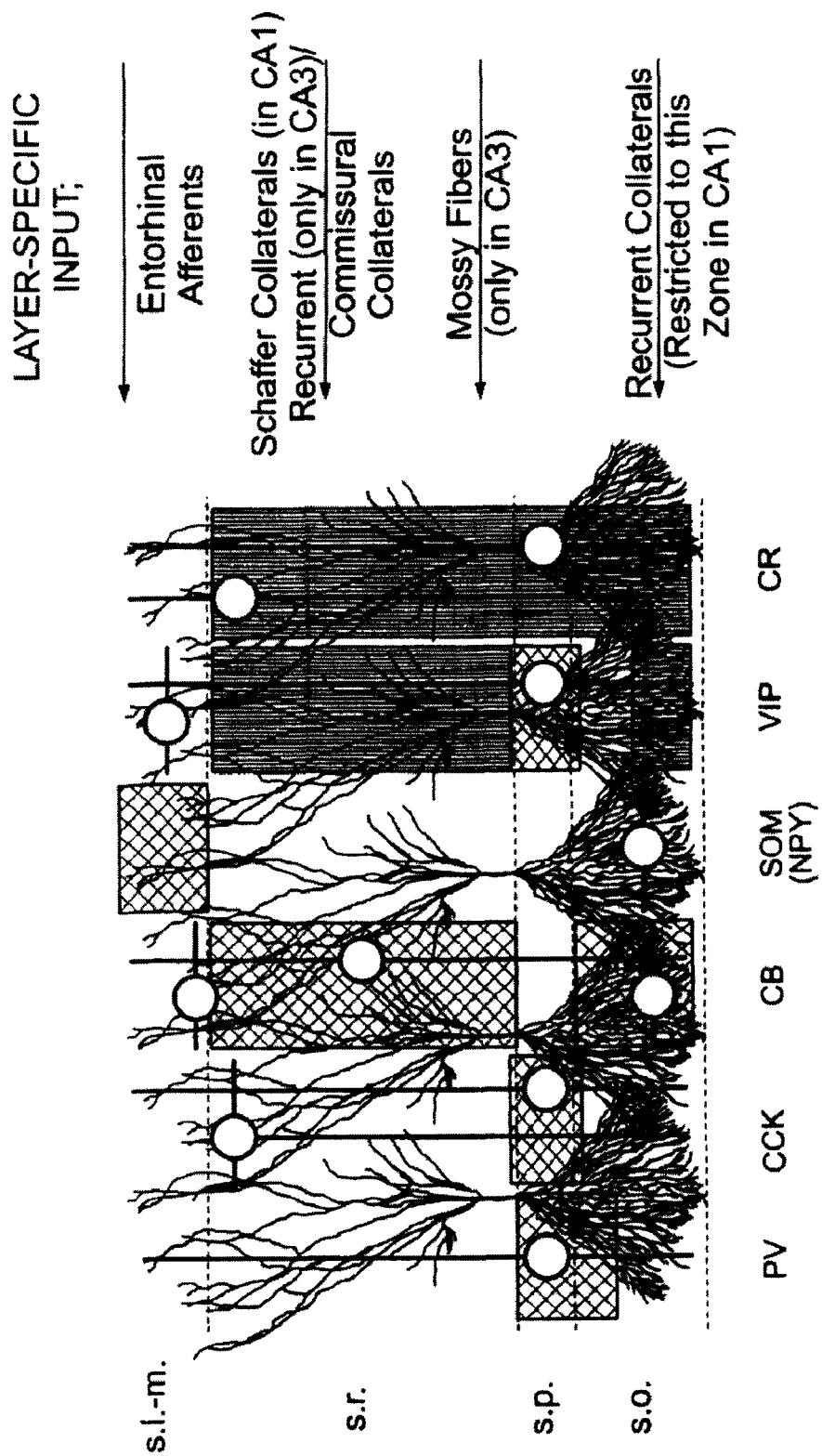
FIG. 19 is a graph indicating axonal and dendritic arborizations of interneuron species.

FIG. 19 summarizes, in graphical form, the axonal and dendritic arborizations of various interneuron species. The dark circles indicate the cell body location of each of the interneuron types; the dark lines emanating from dark circles show the orientation and laminar distribution of the dendritic tree. The hatched boxes shows the layers in which the axons of each interneuron species typically arborize. The vertically striped boxes indicate that other interneurons, rather than pyramidal cells, are the primary targets. Pyramidal cells are shown in outline in the background to provide an idea of which membrane domains (somatic, proximal, or distal dendritic regions) are innervated by the various interneuron types. For example FIG. 19 indicates that PV interneurons project to stratum pyramidale and the proximal area of stratum oriens.

PV cells have been found to be predominantly either basket cells or chandelier cells. In the CA1 subfield, a small number of PV cells have been found to have a bistratified axon projection pattern. Thus, the model assumed that 10% of all PV cells were bistratified, with the remainder evenly divided between basket and chandelier cells.

Certain interneurons stain as both CB and SOM cells. In the computer model, such interneurons were modeled as SOM cells. CB cells are known to innervate the dendrites of pyramidal cells. There are three known subspecies of CB cells, each of which is represented in Table 1. Except for half of the CB cells in the SR, all CB cells were assumed to have a bistratified axonal arborization.

The CR interneurons target the dendritic processes of other interneurons. Therefore, in the model, CR cells were assumed to have an interneuron-projecting arborization, regardless of which layer they were found in.

Within the CA1 hippocampal subfield, SOM cells are believed to be o-lm cells and to have soma within the SO layer. As shown in Table 1, the model also made this assumption.

Virtually all CCK-immunoreactive cells are believed to have a basket axonal aborization. As shown in Table 1, the model made the same assumption.

Finally, PC cells are assumed to populate only the SP layer. All PC cells in the model were assumed to have pyramidal axon arborization.

Having modeled the population of cells in each layer and the morphological category to which they belong, we then modeled the connectivity between neurons. This was done by providing the model with assumption about the targets corresponding to each axonal arborization. Assumptions concerning the targets of an axonal arborization were derived from the studies in which an axon of a particular interneuron type was labeled with an anterigrade tracer to allow visualization of the entire axon with all its ramifications.

Quantitative estimate of spatial synaptic density for each of the interneuron classes were derived from studies in which axonal projections of each of a number of different classes of interneurons were anterigradely stained. On the basis of tissue sections, these studies provided an estimate of a total (linear) axonal distance per volume and a spatial bouton (synapse) frequency, in boutons per length of axon.

In implementing the present model, several simplifying assumptions were made: (i) for a given cell, bouton density was assumed to be a function of the calcium-binding protein of the interneuron, (ii) spatial bouton density was assumed to be invariant with septo-temporal or transverse distance from the parent cell, and (iii) for a given interneuron type, bouton density was assumed to be invariant across strata. The values used in the model, in units of synapses per cubic millimeter were as follows: PV $2.12 \times 10^5$, CB $1.13 \times 10^4$, CR $6.36 \times 10^3$, SOM $4.21 \times 10^5$, CCK $2.12 \times 10^5$.

It is believed that CA1 axons course through the SO toward the alveus, giving off occasional collateral as they do so. Thus, in the new computer model, we assumed that connections between pyramid cells occur only in the SO on the cells basal dendrites. Postsynaptic targets, as pecentages, are not readily available for pyramidal cells. The model thus assumed that the ratio of the number of connections between pyramid cells and the number of connections between pyramid cells and interneurons was roughly proportional to their relative abundance in the SO layer.

Spatial bouton density in pyramidal axons was calculated, as described above in connection with interneurons to be $9.09 \times 10^4$ synapses per cubic millimeter.

Table 2 summarizes the model assumptions concerning connectivity between neurons. Each row in Table 2 corresponds to a type of axon arborization, and each column corresponds to a particular hippocampal layer. At the intersection of a row and column is a 2×3 connectivity matrix that summarizes the connectivity of a particular axon arborizations present in that hippocampal layer.

TABLE 2

| | SO | | | SP | | | SR | | | LM | |
|---|---|---|---|---|---|---|---|---|---|---|---|
| chan | 1 | 0 | 0 | 1 | 0 | 0 | 1 | 0 | 0 | 0 | 0 | 0 |
|  | 0 | 0 | 0 | 0 | 0 | 0 | 0 | 0 | 0 | 0 | 0 | 0 |
| bask | 0 | 0 | 0 | 0.02 | 0.53 | 0.45 | 0 | 0 | 0 | 0 | 0 | 0 |
|  | 0 | 0 | 0 | 0 | 0 | 0 | 0 | 0 | 0 | 0 | 0 | 0 |
| bist | 0 | 0 | 0.93 | 0 | 0 | 0 | 0 | 0 | 0.93 | 0 | 0 | 0 |
|  | 0 | 0 | 0.07 | 0 | 0 | 0 | 0 | 0 | 0.07 | 0 | 0 | 0 |
| intr | 0 | 0 | 0 | 0 | 0 | 0 | 0 | 0 | 0 | 0 | 0 | 0.5 |
|  | 0 | 0 | 1.0 | 0 | 0 | 1.0 | 0 | 0 | 1.0 | 0 | 0 | 0.5 |
| o-lm | 0 | 0 | 0 | 0 | 0 | 0 | 0 | 0 | 0 | 0 | 0.03 | 0.86 |
|  | 0 | 0 | 0 | 0 | 0 | 0 | 0 | 0 | 0 | 0 | 0.11 | 0 |
| radi | 0 | 0 | 0 | 0 | 0 | 0 | 0 | 0 | 0.93 | 0 | 0 | 0 |
|  | 0 | 0 | 0 | 0 | 0 | 0 | 0 | 0 | 0.07 | 0 | 0 | 0 |
| pyra | 0 | 0 | 0.8 | 0 | 0 | 0 | 0 | 0 | 0 | 0 | 0 | 0 |
|  | 0 | 0 | 0.2 | 0 | 0 | 0 | 0 | 0 | 0 | 0 | 0 | 0 |

The first row of each connectivity matrix provides data on how the particular axon arborization connects to pyramid cells, and the second row provides data on how that axon arborization connects to interneurons. The three columns in the connectivity matrix correspond to different parts of the target cell to which the particular axon arborization can connect. From left to right, these are the initial segment, the soma, and the dendrites.

For example, Table 2 shows that in the model, a bistratified axon arborization present in the SO layer was assumed to connect to a dendrite on a pyramid cell with probability 0.93, and to connect to a dendrite on an interneuron with probability 0.07. Basket axon arborizations were assumed to exist only in the SP layer and to connect only to pyramid cells. Within the SP layer, the basket axon arborization can connect to all three parts of the pyramid cell, but only rarely to its initial segment (with probability 0.2).

The model assumptions shown in Table 2 were derived from known studies in which axons of a particular interneuron type were labeled with an anterograde tracer, allowing visualization of the entire axon with all of its ramifications. For example, it is known that o-lm cells project only to LM; that of the total number of synaptic connections they form there, 86% are on dendrites of pyramidal cells, 3% are on pryamidal cell soma, and 11% are on interneuron soma. Analogous data has been derived from similar experiments on the other interneuron classes.

Data underlying Table 2 can be found in a variety of publications. For example, *Katona*, et al., "Postsynaptic targets of somatostatin-immunoreactive interneurons in the rat Hippocampus," Neuroscience, 1999, 88(1):37-55 reports that o-lm cells project only to the LM, and that of the total number of synaptic connections they form there, 86% are on dendrites of pyramidal cells, 3% are on pyramidal cell somata, and 11% are on interneuron somata. Similar data for basket cells is found in *Halasy*, et al., "Synaptic Target Selectivity and Input of GABAergic Basket and Bistatified Interneurons in the CA1 Area of the Rat Hippocampus," Hippocampus, 1996, 6:306-329. Data for bistratified cells is found in *Gulyas*, et al., "Pyramidal cell dendrites are the primary targets of calbindin D28k-immunoreactive interneurons in the hippocampus," Hippocampus, 1996, 6(5):525-34. Data for oriens-lacunosum-moleculare cells is also found in *Katona*, et al., cited above. Data for pyramidal cells is found in *Somogyi, P.*, et al., "Salient features of synaptic organization in the cerebral cortex," Brain Research Reviews, 1998, 26:113-135. Regarding interneuron-projecting cells, *Gulyas* et al., "Interneurons containing calretinin are specialized to control other interneurons in the rat hippocampus," J. Neurosci, 1996, 16(10):3397-411 states that CR interneurons synapse with dendrites of other interneurons.

Because of constraints on the data structure used in implementing the model, certain simplifying assumptions were made. For example, it is believed that CR interneurons synapse with dendrites of other interneurons, with the following caveats: (a) CB interneurons avoid PV interneurons; (b) when CR interneurons contact other CR interneurons, they do so at both dendrites and at soma; and (c) CR interneurons form dendro-dendritic contacts (gap junctions) with one another. These subleties were ignored in the present model, in part because of a paucity of experimental data for incorporating into the model.

In addition to modeling the population of neurons and their steric relationships, were also modeled synaptic connections. In the new model, this synaptic conductance was assumed to obey the function $$g_{syn}(t) = \frac{Ag_{max}}{\tau_1 - \tau_2}(e^{-1/\tau_1} - e^{-1/\tau_2}), \text{ for } \tau_1 > \tau_2,$$

where $\tau_1$ and $\tau_2$ are time constants associated with the synapse and A is a normalization constant chosen such that $g_{sym}$ reaches a maximum of $g_{max}$.

At the GENESIS level, neurotransmitter release into the synaptic cleft is not explicitly modeled. Rather, the synchan object is placed postsynaptically. When a "SPIKE" message is received by the synchan object, it activates according to parameters set in its fields.

All interneurons form GABAergic level, neutransmitter release into the synaptic cleft is not explicitly modeled. Rather, the synchan object is placed postsynaptically. When a "SPIKE" message is received by the synchan object, it activates according to parameters set in its fields.

All interneurons form GABAergic synapses on their target cells. Pyramidal cells form excitatory synapses on their target cells, either AMPA or NMDA, with a 0.5 probability for each. Channel characteristics, in terms of values given in the foregoing equation, are presented in Table 3.

TABLE 3

| | E(volts) | $\tau_1$ (sec) | $\tau_2$ (sec) | gmax (nS) |
|---|---|---|---|---|
| AMPAp | 0 | 0.0536 | 0.00132 | 8 |
| NMDAp | 0 | 0.1440 | 0.00100 | 6 |
| GABAp | -0.075 | 0.0094 | 0.00100 | 3 |
| AMPAi | 0 | 0.0536 | 0.00132 | 6 |

TABLE 3-continued

|  | E(volts) | $\tau_1$ (sec) | $\tau_2$ (sec) | gmax (nS) |
|---|---|---|---|---|
| NMDAi | 0 | 0.0540 | 0.00130 | 2 |
| GABAi | −0.075 | 0.0094 | 0.00100 | 0.5 |

In the computer model, all synaptic stimulatation to cells (except for the initial stimulation) arose from cells within the model. Because the model represented only a very small piece of tissue, the innervation of a typical cell in the model was considerably lower that that of hippocampal cells in vivo. For example, actual CA pyramidal cells receive about 30,000 excitatory and 1,700 inhibitory inputs, which is orders of magnitude greater than the number of synaptic inputs received by pryamidal cells in the present model. To compensate, $g_{max}$ for all synaptic conductances was weighted by a dimensionless scale factor. the weight factor was obtained experimentally by gradually increasing it and re-running the computer model until pyramidal interneuron outputs showed realistic spike waveforms. A suitable weight factor for the foregoing computer model was 300.

Initial Stimulus

A computer model of neural tissue, no matter how realistic, will do nothing unless it receives an initial stimulus. Once subjected to a stimulus, the computer model evolves through a series of states. This evolution depends on the various parameters defined above.

In the present example, the initial excitation was selected to be biologically realistic, but not necessarily to contain any information. The initial excitation chosen was to set all potentials to zero and then to excite each neuron for one second using a pulse sequence having a mean frequency of 15 Hz. The excitation frequency and phase were both random to avoid the possibly unrealistic effect of synchronicity between neurons. The simulated trans-membrane potentials in each neuron in the model were periodically recorded.

Output from Normal Model

The foregoing pattern of initial excitation produced an initial transient period that lasted approximately 0.5 seconds. Following this transient period, the simulated neuron potentials settled into a normal pattern of spike waveforms. Data from this transient period was excluded from out analysis because such data would not have been biologically realistic.

The raw output provided by the model after simulation included 452 time-varying voltages. Because of difficulty inherent in interpreting such copious data, it was useful to implant "virtual electrodes" at 16 locations throughout the simulated tissue block to record local field potentials averaged over a volume of tissue. The virtual electrodes were created by summing local field potentials at points surrounding the desired location of the virtual electrode. The output of such a virtual electrode was given by a sum of local field potentials at discrete points weighted by the distances between the discrete points and the location of the virtual electrode:

$$\Phi = \frac{1}{4\pi s} \sum_{i=1}^{n} \frac{I_{mi}}{R_t}$$

where $\Phi$ is the field potential in volts, s is conductivity of the medium surrounding the neurons (in mhos), $I_{mi}$ is the trans-membrane current (in amperes) across the $i^{th}$ neural compartment, and $R_t$ is the distance from the $i^{th}$ neural compartment to the virtual electrode. The sum was evaluated over every computational compartment of every neuron in the simulation.

Table 4 compares the average spike rates (in Hertz) in the model with approximate spike rates (also in Hertz) as measured in rats engaged in a variety of tasks. These tasks include performing trials on radial 8-arm maze task (column "a"); paradoxical sleeping (column "b"), slow-wave sleeping (column "c"), and being in a "maximum" behavioral state (column "d").

TABLE 4

|  | model | (a) | (b) | (c) | (d) |
|---|---|---|---|---|---|
| pyramidals | 2.45 | 2 | 0.1-0 | 0.5-5 | <20 |
| interneurons | 25.6 | 15 | 30-100 | 10-40 | 30-100 |

The average spike rate for all pyramidal cells in the model was on the order of 2.45 Hz, and for all interneurons to be 25.6 Hz. Of the 452 cells in the model, 122 spiked at least once during the simulation. This is consistent with published results for corresponding in vivo spike rates.

Figure 20A:
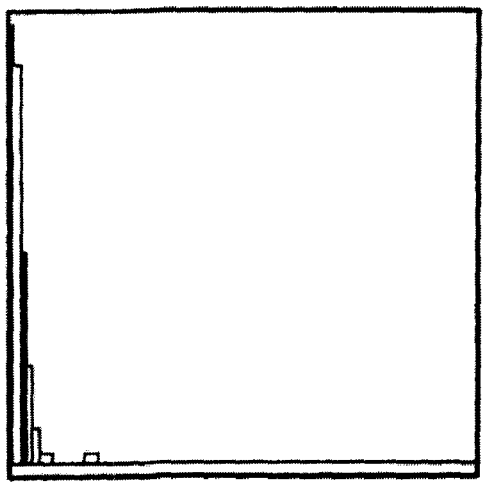
FIGS. 20A and 20B are graphs comparing modeled and measured spike rates for interneurons.
Figure 20B:
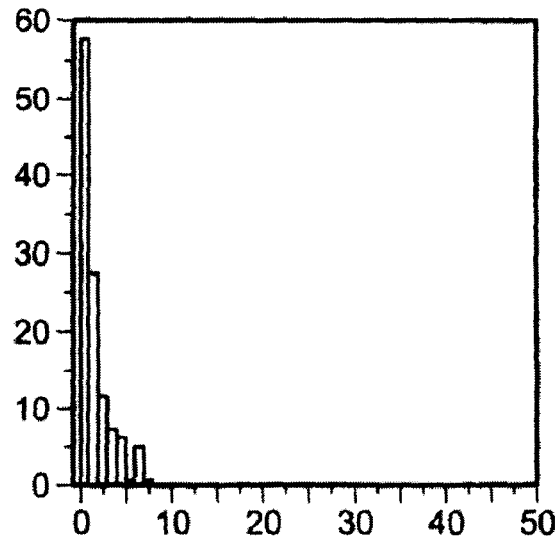
Figure 20C:
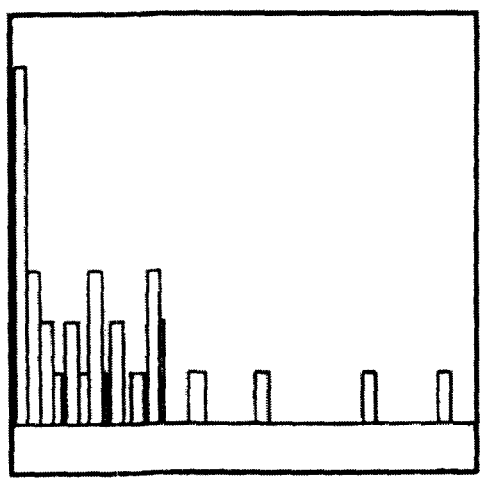
FIGS. 20C and 20D are graphs comparing modeled and measured spike rates for interneurons.
Figure 20D:
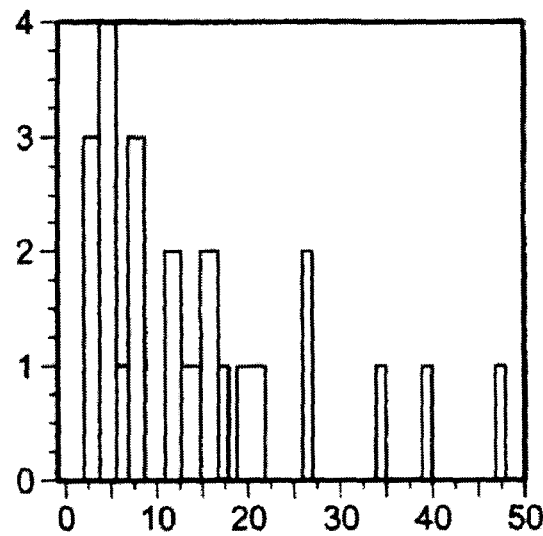

The distribution of spike rates in vivo also matches the corresponding distribution of spike rates in the model. For example, FIG. 20A shows a histogram distribution of spike rate for pyramidal cells in the model. FIG. 20B shows a histogram of corresponding spike rates as measured in vivo in a rat hippocampus. FIG. 20C and 20D are corresponding histograms for interneuron spike rates in both the computer model (FIG. 20C) and in the rat (FIG. 20D).

Figure 21A:
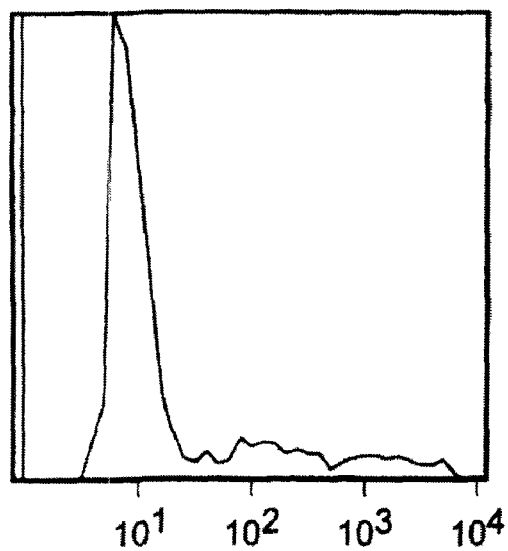
FIGS. 21A and 21B are graphs comparing modeled and measured inter-spike intervals for pyramidal cells.
Figure 21C:
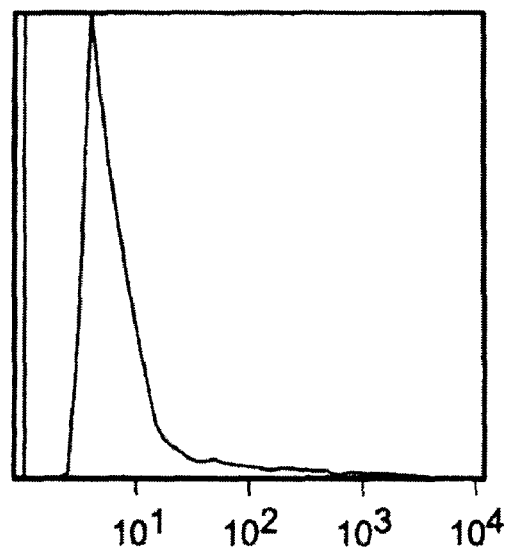
FIGS. 21C and 21D are graphs comparing modeled and measured inter-spike intervals for interneurons.
Figure 21B:
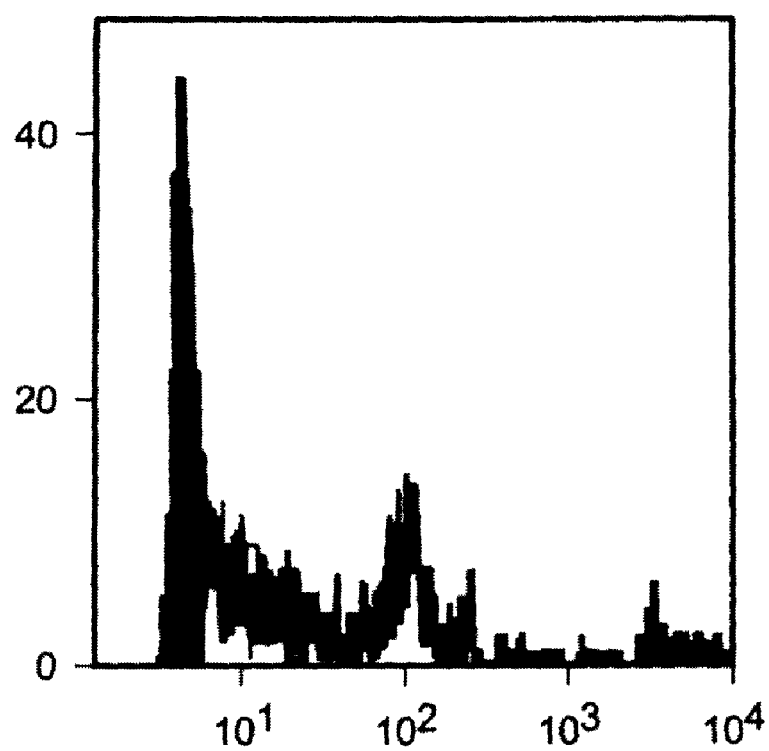
Figure 21D:
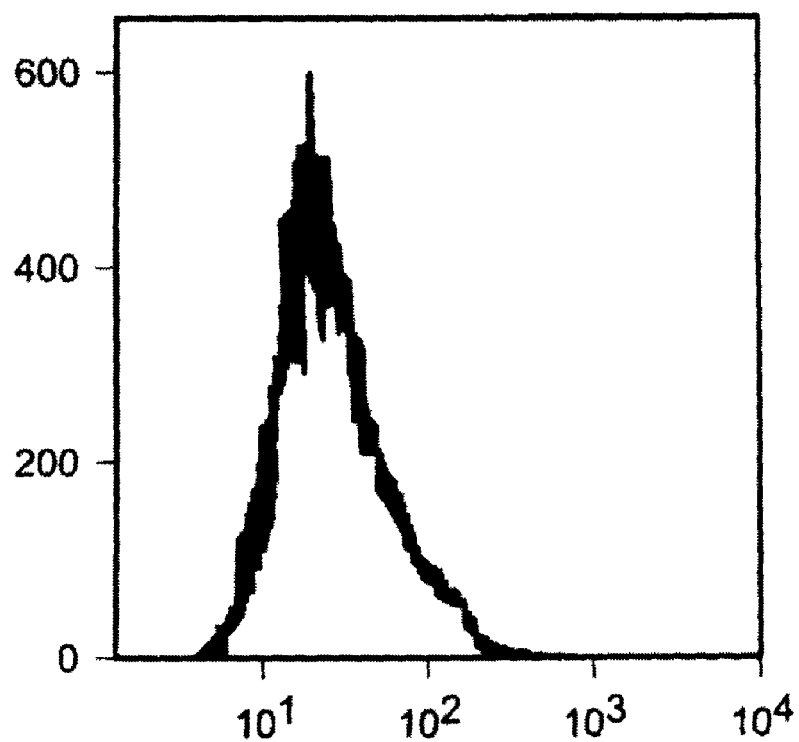

The distribution of intervals between spikes in vivo also matches the corresponding distribution of intervals in the model. For example, FIGS. 21A-21D show the distributions of the intervals between spikes for pyramid cells (FIGS. 21A-21B) and interneurons (FIGS. 21C-21D). FIGS 21B and 21D show measured interval distributions as measured in vivo from a rat hippocampus, and FIGS. 21A and 21C show modeled interval distributions. Comparison of these figures indicates that the interval distribution of the model matches that obtained in vivo.

Figure 22A:
FIG. 22A is a graph of the output of a virtual electrode in a model of a normal hippocampus.
Figure 22B:
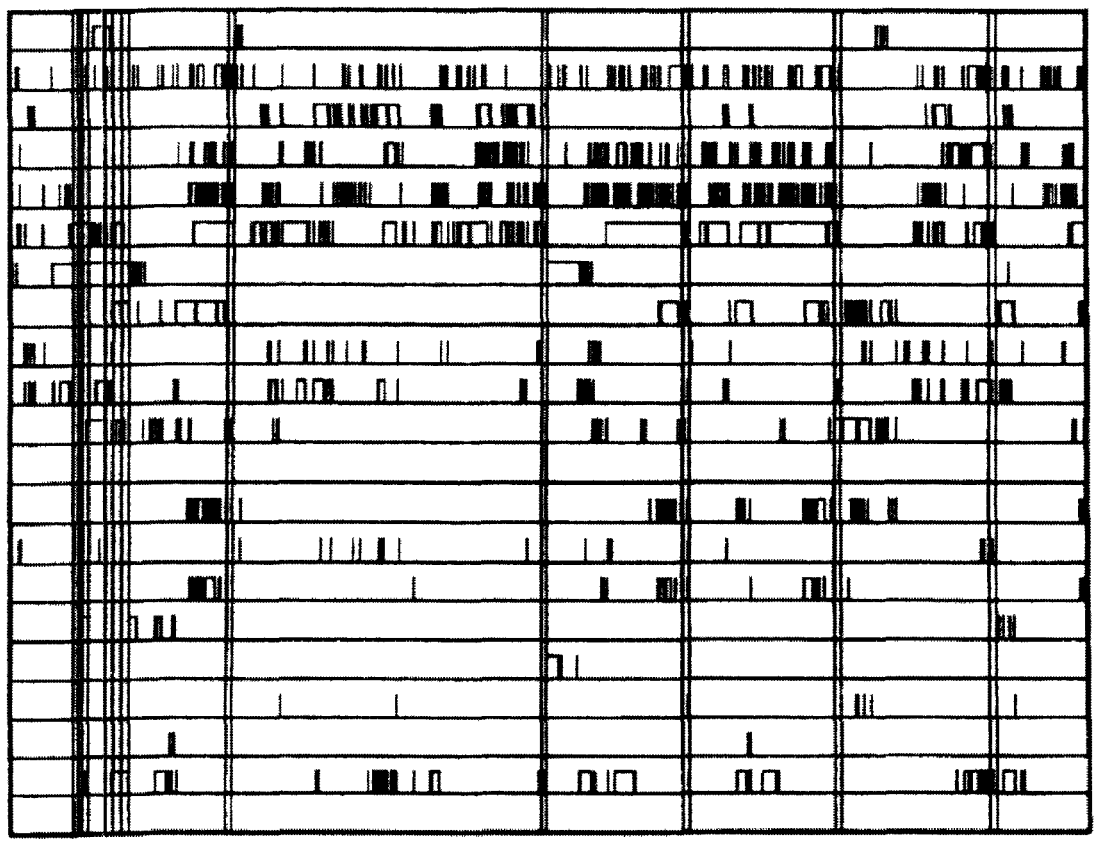
FIG. 22B is a graph of a firing pattern of neurons from a model of a normal hippocampus.

By observing the evolution of the spatial distribution of voltage potentials over all the neurons, it was possible to identify activity "epochs" of relative stability, separated by short transition periods. In FIG. 22B, a firing pattern for a subset of twenty neurons reveals a number of these stable epochs. The lengths of these epochs did not appear to change for small changes in the parameters of the model.

Inspection of the spike train of a single neuron in many cases revealed episodes of fast firing followed by episodes of markedly slower firing. Using this data, we defined a transition point as occurring when the sequential inter-spike interval ratio (ISI(t)/ISI(t+1)) was either very large, indicating the beginning of a fast-spiking episode, or very small, indicating end of such an episode. When a sufficient number (referred to as a "threshold number") of neurons experienced a transition point within an adequately narrow time window, a transition between activity epochs was said to occur. When using parameter values for sequential ISI ratio, threshold, and time window of 14, 10, and 33 msec, respectively, the system exhibited seven transitions, which defined eight activity epochs. This behavior was robust to small changes in parameter values. It was seen, to a greater or lesser degree, in all local field potentials measured by all the virtual electrodes in the model. A representative trace, from a virtual electrode in the stratum pyramidale is shown in FIG. 22A.

Figure 23:
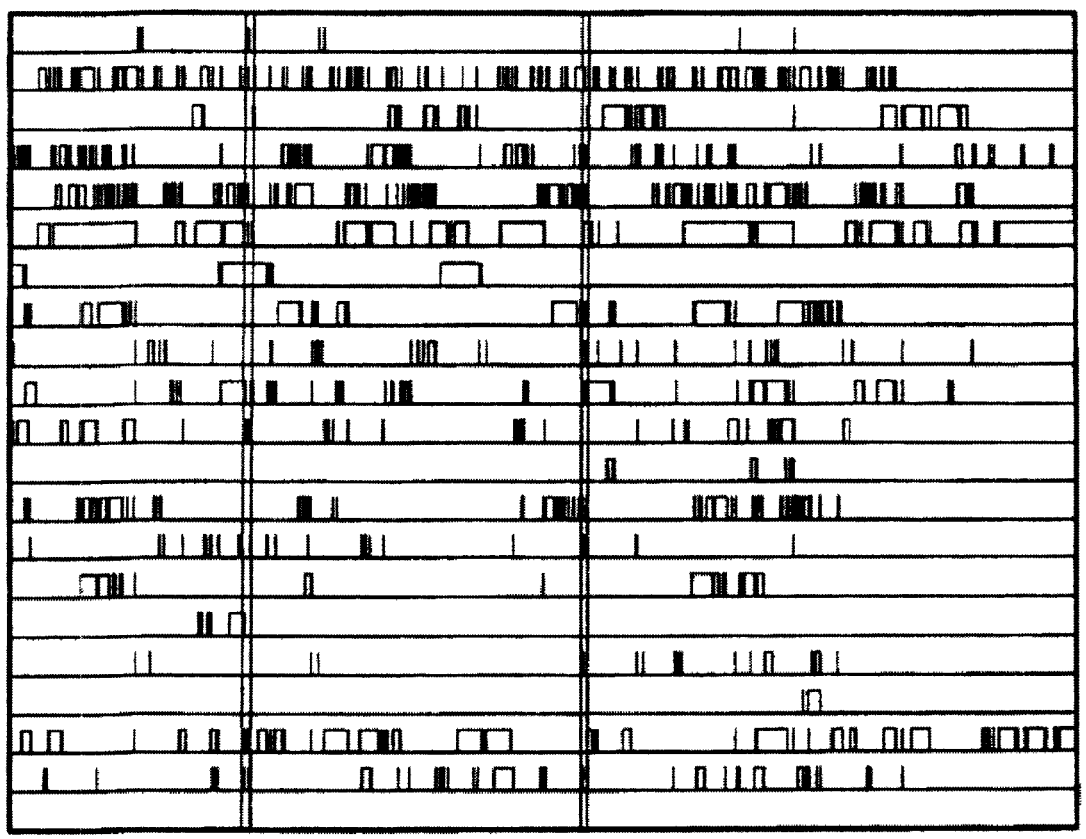
FIG. 23 is a graph of a neuron firing pattern from a model of a hippocampus with $I_{AHP}$ channels removed.

Inspection of the data indicated that many transitions between epochs were preceded by the progressively slower firing of a number of cells. This is consistent with spike frequency adaptation (SFA), a process that is mediated by slow Ca$^+$-activated K$^+$ channels. Removing the $I_{AHP}$ channels from the constituent meurons of the hippocampus model disables SFA. When this was done, and the model subjected to the same initial excitation, only three activity epochs were present in the same time period. A portion of the resulting firing pattern is shown in FIG. 23.

The stable states, or epochs, behave consistently with the attractor states described in the neural network literature. As discussed earlier, in a neural network, attractors are stable fixed points of the system that correspond to minima of the network's energy function over all values of its state-space. It has been theorized that these states, occurring in biological neural tissue, represent memories. Hence, the matrix of neural connections is the storage medium for these memories.

It is therefore useful to consider whether the epochs are in fact attractors. To do so, we defined a weight matrix, W, and an input vector $\vec{V}_{ni}$.

The weight matrix was a 452×452 element array W of elements $W_{ij}$. Each $W_{ij}$ represented the strength of synaptic stimulation (excitatory or inhibitory) that neuron i exerted on neuron j. For example, if neuron i were a pyramidal cell that sent x synaptic contacts to neuron j, then $W_{ij}$ would have been x. If neuron i were instead an interneuron, then $W_{ij}$ would have been −x.

The input vector $\vec{V}_{ni}$ had the same number of elements as there were neurons in the model (in this case 452 elements). This vector represented the normalized activation pattern of all cells in the system during a particular epoch, n. $\vec{V}_{ni}$ was obtained by calculating the spike rate of cell i during epoch n, then normalizing the spike rates of all cells so that all elements of $\vec{V}_{ni}$ lay in the interval [0,1]. This was consistent with the assumption of rate-coded information.

The simulation was implemented using the GENESIS neural modeling language and run under LINUX on a dual-processor PC as described in Bower, J. M. and D. Beeman, *The Book of GENESIS: Exploring Realistic Neural Models with the GEneral NEural SImulation System*, 1995, Santa Clara, Calif. The individual pyramidal cell and interneuron models were ported to GENESIS by Sampat and Huerta and Menschik and Finkel, respectively. Both models are available on the internet at genesis-sim.org/BABEL/babeldirs/cells. C programs to specify cell placement and connectivity are designed to read parameter files in the form presented in Tables 1 and 2. This allows the model to be updated as additional neuroanatomic information becomes available. In addition, this allows the model to be selectively altered to simulate the effects of lesioning.

Example 3

Computer Model of Schizophrenic Hippocampus

Although the neuropathological lesion of schizophrenia is not know with certainty, postmortem studies on the hippocampi of human schizophrenics indicate abnormalities in writing distribution of cell types, particularly interneurons, and in particular, PV interneurons. On the basis of this published data, schizophrenia was simulated by reducing the population of interneurons by 56%. The interneurons removed were PV interneurons because it is believed that the hippocamus of a schizophrenic has fewer such interneurons. The resulting model will be referred to as the "schizophrenic model."

The remaining interneurons may show subtle changes in connectivity. These changes can be incorporated in the model by altering the data in Table 2. However, any such changes in connectivity remain unaccounted for in the present model of the schizophrenic hippocampus, in part because of a paucity of suitable experimental data.

When the schizophrenic model was re-executed with the same initial stimulus as was applied to the normal model, the number of epochs observed during the run time was reduced from eight to two. This suggested that the frequency of such stable epochs was associated with the presence of schizophrenia.

Figure 24:
FIG. 24 is a graph of neuron firing patterns from a model of schizophrenic hippocampus.

Representative data following application of the stimulus to the schizophrenic model is shown in FIG. 24. Unlike the 5.5 seconds of firing data shown in FIGS. 22B and FIG. 23, FIG. 24 shows only 4.5 seconds of firing data. In addition, the neurons shown in FIG. 24 are primarily pyramidal cells, whereas the neurons shown in FIGS. 22B and 23 are primarily interneurons. Nevertheless, it is clear that the firing pattern in FIG. 24 shows many fewer epochs than does the firing pattern in FIG. 22B. This result indicates that the frequency of transitions between epochs, or equivalently the frequency of epochs may correlate with the presence of schizophrenia. In particular, a lower epoch frequency appears to be associated with schizophrenia. As such, a test composition that increase the epoch frequency potentially an effective treatment for schizophrenia.

Example 4

Computer Model of Chlorpromazine-Treated Schizophrenic Hippocampus

If, for a given compound, receptor affinities, intracellular effector mechanisms, and ultimate effects on ion channel functioning are known, then the methods outlined above can be used. However, even if these parameters are unknown, drug effects can be supplied, as shown in this Example and Example 5.

The effect of chlorpromazine on neural tissue was modeled by chaning the conductances of the ion channels of each neuron. A computational model of the manner in which the conductance of sodium and potassium ion channels change with respect to time and voltage is given by equations 4.8-4.9 in the *Book of Genesis* (supra) as follows:

$$G_{Na} = \vec{g}_{Na} m^3 h \text{ and}$$

$$G_k = \vec{g}_k n^4$$

$$G_{Ca} = \vec{g} m^2 h$$

The conductances of a sodium channel, for example, is the product of a constant term $\vec{g}_{Na}$, and two time-varying terms, $m^3$ and h. A computational model of the time-variation of these terms and their voltage dependence is given by equations 4.11-4.13 in the *Book of Genesis*:

$$\frac{dm}{dt} = \alpha_m(V)(1-m) - \beta_m(V)m$$

$$\frac{dh}{dt} = \alpha_h(V)(1-h) - \beta_h(V)h$$

$$\frac{dn}{dt} = \alpha_n(V)(1-n) - \beta_n(V)n$$

The functional form of the alpha(V) and beta(V) term are given by equations 4.21 and 4.22 in the *Book of Genesis*:

$$\alpha_n(V) = \frac{n_\infty(V)}{\tau_n(V)}$$

$$\beta_n(V) = \frac{1 - n_\infty(V)}{\tau_n(V)}$$

In GENESIS, most ion channels are implemented using the "tabchannel" object. This object allows specifications of such fields as $\vec{g}$, and for specifying the α and β functions.

A computer model of neural tissue exposed to chlorpromazine was obtained by altering the constant term of the conductance equation shown above. In particular, the schizophrenic model is altered by:

halving the value of $\vec{g}_{Na}$ for all sodium ion channels;

by multiplying the $\vec{g}_{Ca}$ value for all calcium ion channels by 0.71;

by multiplying the $\vec{g}_k$ value associated with the sustained potassium current ($I_A$ or $K_A$) channel by 0.6.

For interneurons, $\vec{g}_{Na}$ was set to 0.0349 siemens, $\vec{g}_k$ was set to 0.0174 siemens, and $\vec{g}_{Ca}$ was set to 0.0047. For pyramidal cell, $\vec{g}_{Na}$ was set to 0.1229 siemens, $\vec{g}_k$ was set to 0.0615 siemens, and $\vec{g}_{Ca}$ was set to 0.0164 siemens.

As data on the time-varying effect of chlorpromazine becomes available, the computer model can be further enhanced by altering the time-varying term consistent with that data.

Figure 25:
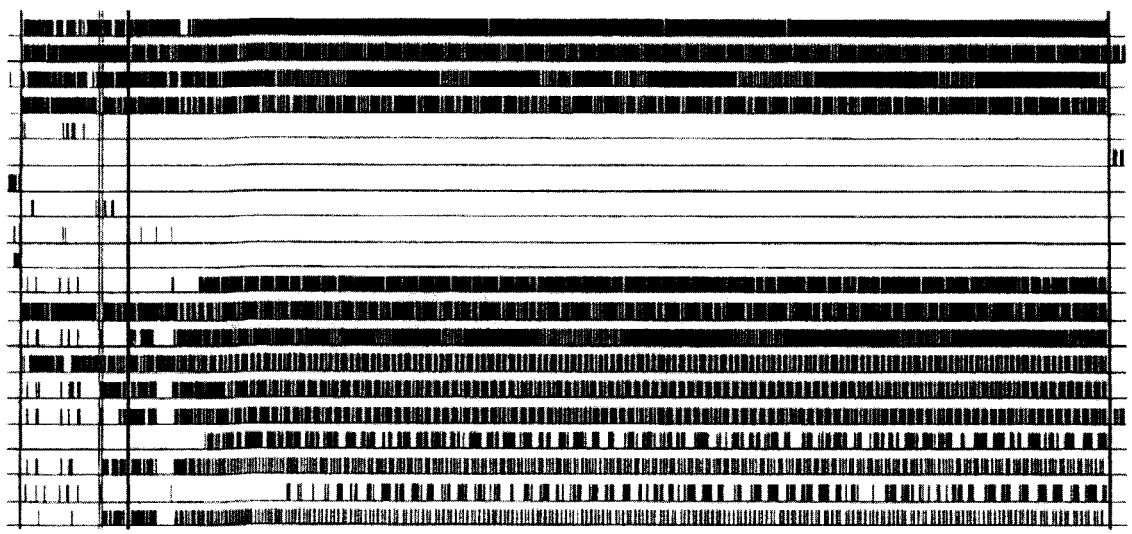
FIG. 25 is a graph of neuron firing patterns from the hippocampus model of FIG. 24 after having been treated with a psychiatric drug.

The result of re-executing the model with the foregoing changes is shown in FIG. 25. Comparison of FIGS. 24 and 25 shows that the number of stable epochs is increased from three in FIG. 24 to five in FIG. 25. This suggests that chlorpromazine affects the neural tissue of the schizophrenic model in a way that drives it toward normalcy.

Example 5

Model of Drugs that Act on Receptors

Not all psychiatric drugs are amenable to modeling by altering ion channel conductances as described above. For other psychiatric drugs, only the effect on neurotransmitter receptors is known. If a drug is known to block a particular dopamine receptor with a known affinity, one can alter the model to simulate this effect. The method described in this example can be brought to bear if a receptor's ultimate effects are not mediated by intracellular messaging, or the details of such messaging pathways are not completely understood.

In particular, affinities of many drugs for receptors are well known. For example, *Goodman and Gilmans* "The Pharmacological Basis of Therapeutics," Tenth Edition. McGraw-Hill, 2001, list such affinites. The following equation, from *Cooper, J. R.* et al., "The Biochemical Basis of Neuropharmacology," Seventh Ed., Oxford University Press, 1996, gives the fraction of receptors occupied (r) as function of concentration of drug ([L]) and a dissociation constant Ki.

$$r = \frac{[L]}{[L] + Ki}$$

The Ki value, which is inversely proportional to affinity, is the concentration needed to saturate half of the receptor. In Table 20-2 (entitled "Potencies of Standard and Experimental Antipsychotic Agents at Neurotransmitter Receptors") of Goodman and Gilman's (supra), Ki is given in nanomolar (nM) quantities.

To model the effect of olanzapine on the K+channel via its antagonism of the D1 receptor, one first obtains olanzapine's Ki for the D1 receptor, which is 31.0. A reasonable value for the free concentration of olanzapine (corrected for binding to plasma proteins) is 27 nM. This value is from *Tran*, et al, "Olanzapine (Zyprexa)—A Novel Antipsychotic," Lippincott Williams and wilkins, 2000. The fraction of occupied receptors, r, is therefore is 0.47.

From *Kuzhikandathil, E. V. and Oxford, G. S.*, "Classic D1 dopamine receptor antagonist R-(+)-7-chloro-8-hydroxy-3-methyl-1-phenyl-2,3,4,5-tetrahydro-1H-3-benzazepine hydrochloride (SCH23390) directly inhibits G protein-coupled inwardly rectifying potassium channels,*" Molecular Pharmacology.* 62(1):119-26, 2002, we see that complete D1 antagonism results in a decrease in the magnitude of the K+ current by about 30%. Similar data is available for many receptor-ion channel combinations.

Statistically, approximately 47% of D1 receptors will be blocke (antagonized) at a therapeutic olanzapine level. Therefore, the complete D1 antagonist effect described above is corrected by this amount by decreasing the constant ($\vec{g}$) term in the equation for conductance. Thus, the baseline $\vec{g}$ is weighted by 0.30×0.47 to arrive at the $\vec{g}$ value for the olanzapine treated neuron.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A computer-implemented method for screening a receptor antagonist test composition for potential efficacy in treatment of schizophrenia, the method comprising causing a computer to execute instructions for:
   (a) creating a first computer model representative of a volume of disease-afflicted neural tissue comprising a plurality of interconnected modeled neurons; wherein for each modeled neuron the model quantitatively simulates spatially compartmentalized conductance of a plurality of ion channels and spatially compartmentalized activity of a plurality of receptors;
   (b) modifying the first computer model to simulate exposure of each of the receptors R in the disease-afflicted neural tissue to the test composition by
      (1) defining (i) an antagonist test composition concentration B, (ii) an antagonist test composition dissociation constant $K_B$, (iii) a naturally present agonist concentration A, (iv) a naturally present agonist dissociation constant $K_A$, (v) a receptor concentration $R_t$, (vi) an equilibrium dissociation constant $K_A$, and (vii) an efficacy constant $K_E$;
      (2) calculating for each receptor R in the model a fractional occupancy of the receptor by naturally present agonist A in the presence of antagonist test composition B using equation (1):

$$\frac{[A \cdot R]}{[R_t]} = \frac{[A]}{[A] + K_A(1 + [B]/K_B)} \quad (1)$$

wherein A·R represents a concentration of an agonist-receptor complex;

(3) using the value of A·R from step (2), calculating a test composition response ratio $E_a/E_m$ for each receptor in the model using equation (2):

$$\frac{E_a}{E_m} = \frac{[A \cdot R]}{K_E + [A \cdot R]} \quad (2)$$

wherein $E_a$ is a test composition response and $E_m$ is a maximal test composition response; and (4) combining results for each receptor in the model to provide an overall test composition efficacy;

(c) providing an initial excitation to the first modified computer model;

(d) determining a first outcome indicative of a response of the first modified computer model to the initial excitation and the test composition, wherein the first outcome is representative of the efficacy of the test composition at treating the disorder; and (e) providing an output indicative of the efficacy of the test composition at treating the disorder to a physical memory, a mass storage device, a removable media, or a user interface device.

2. The method of claim 1, further comprising:
creating a second computer model representative of the volume of disease-afflicted neural tissue comprising a plurality of interconnected modeled neurons each comprising a dendro-somatic axis; wherein the volume is isolated from the test composition; and wherein for each modeled neuron the model quantitatively simulates spatially compartmentalized conductance of a plurality of ion channels and spatially compartmentalized activity of a plurality of receptors; and wherein each modeled neuron is generated from data describing two or more of (1) a distribution of neuroreceptors along the dendro-somatic axis; (2) an anatomically realistic dendritic arborization pattern, and (3) a density of ion channels present along the dendro-somatic axis;
providing the initial excitation to the second computer model;
determining a second outcome indicative of a response of the volume of disease-afflicted neural tissue represented by the second computer model to the initial excitation; and
classifying the test composition as a candidate composition for treating the disorder on the basis of a difference between the first and second outcomes.

3. The method of claim 1, further comprising:
creating a second computer model representative of the volume of disease-afflicted neural tissue comprising a plurality of interconnected modeled neurons each comprising a dendro-somatic axis; wherein the volume is isolated from the test composition; and wherein for each modeled neuron the model quantitatively simulates spatially compartmentalized conductance of a plurality of ion channels and spatially compartmentalized activity of a plurality of receptors;
providing the initial excitation to the second computer model;
determining a second outcome indicative of a response of the volume of disease-afflicted neural tissue represented by the second computer model to the initial excitation; and classifying the test composition as a candidate composition for treating the disorder on the basis of a difference between the first and second outcomes.

4. The method of claim 1, further comprising:
creating a second computer model representative of the volume of neural tissue, wherein the neural tissue is free of the disease and comprises a plurality of interconnected neurons, wherein for each neuron, the model quantitatively simulates spatially compartmentalized conductance of a plurality of ion channels and spatially compartmentalized activity of a plurality of receptors;
providing the initial excitation to the second computer model; and
determining a second outcome indicative of a response of the volume of disease-free neural tissue represented by the second computer model to the initial excitation; and
classifying the test composition as a candidate composition for treating the disorder on the basis of a similarity between the first and second outcomes.

5. The method of claim 4, further comprising:
determining a first epoch frequency associated with the first outcome;
determining a test epoch frequency associated with the second outcome; and
classifying the test composition as a candidate composition for treatment of the disorder on the basis of a relationship between the first epoch frequency and the test epoch frequency.

6. The method of claim 1, further comprising selecting the volume to be a volume of a hippocampus.

7. A computer system for screening a test composition, the system comprising:
a processor;
a storage medium coupled to the processor, the storage medium encoding software that, when executed, causes the processor to carry out the method of claim 1.

8. A computer-readable medium having encoded thereon software functionally interacting with a system for screening a test composition for potential efficacy in treatment of a disorder, the software comprising instructions for causing the system to carry out the method of claim 1; wherein the computer-readable medium comprises a memory in a computer, a mass storage component, or a media that can be inserted or removed from a computer.

9. The method of claim 2, further comprising:
creating a third computer model representative of the volume of neural tissue, wherein the neural tissue is free of the disease and comprises a plurality of interconnected neurons, wherein for each neuron, the model quantitatively simulates spatially compartmentalized conductance of a plurality of ion channels and spatially compartmentalized activity of a plurality of receptors;
providing the initial excitation to the third computer model; and
determining a third outcome indicative of a response of the volume of disease-free neural tissue represented by the third computer model to the initial excitation; and
classifying the test composition as a candidate composition for treating the disorder on the basis of a similarity between the first and third outcomes.

* * * * *

UNITED STATES PATENT AND TRADEMARK OFFICE
CERTIFICATE OF CORRECTION

PATENT NO. : 7,945,392 B2  
APPLICATION NO. : 11/559611  
DATED : May 17, 2011  
INVENTOR(S) : Peter Siekmeier and Steven Matthysse It is certified that error appears in the above-identified patent and that said Letters Patent is hereby corrected as shown below:

On the Title Page,

Item (56) line 18, Other Publications, delete "Artifical" and insert -- Artificial --.

Item (57) Abstract, after "includes" insert -- creating --.

Signed and Sealed this
Ninth Day of August, 2011

David J. Kappos
*Director of the United States Patent and Trademark Office*